United States Patent
Venet et al.

[11] Patent Number: 5,968,952
[45] Date of Patent: Oct. 19, 1999

[54] FARNESYL TRANSFERASE INHIBITING 2-QUINOLONE DERIVATIVES

[75] Inventors: Marc Gaston Venet, Le Mesnil Esnard; Patrick René Angibaud, Fontaine-Bellenger; Gérard Charles Sanz, Le Mesnil Esnard, all of France; David William End, Ambler, Pa.

[73] Assignee: Janssen Pharmaceutica, N.V., Beerse, Belgium

[21] Appl. No.: 09/066,441

[22] PCT Filed: Oct. 25, 1996

[86] PCT No.: PCT/EP96/04661

§ 371 Date: Apr. 29, 1998

§ 102(e) Date: Apr. 29, 1998

[87] PCT Pub. No.: WO97/16443

PCT Pub. Date: May 9, 1997

[30] Foreign Application Priority Data

Oct. 31, 1995 [EP] European Pat. Off. ............. 95202945

[51] Int. Cl.$^6$ ..................... C07D 215/16; C07D 215/04; C07D 215/12

[52] U.S. Cl. ..................... 514/312; 514/311; 514/314; 546/154; 546/157; 546/158; 546/173; 546/176

[58] Field of Search ..................... 514/311, 312, 514/314; 546/154, 157, 158, 173, 176

[56] References Cited

FOREIGN PATENT DOCUMENTS

| | | |
|---|---|---|
| 0 371 559 | 6/1990 | European Pat. Off. . |
| 0 371 564 | 6/1990 | European Pat. Off. . |
| 0 574 992 A1 | 12/1993 | European Pat. Off. . |
| 0 677 513 A1 | 10/1995 | European Pat. Off. . |

*Primary Examiner*—D Margaret M Mach
*Attorney, Agent, or Firm*—Mary A. Appollina

[57] ABSTRACT

The present invention is concerned with compounds of formula (I),

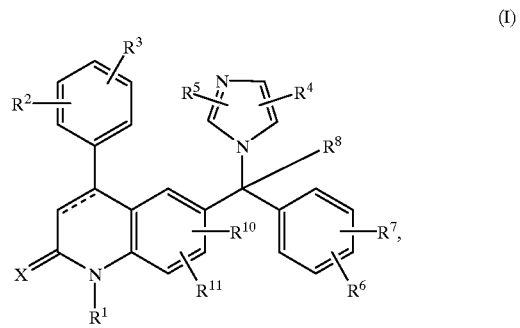

(I)

the stereoisomeric forms thereof and the pharmaceutically acceptable acid or base addition salts thereof, wherein the dotted line represents an optional bond; X is oxygen or sulfur; $R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)-amino$C_{1-6}$alkyl, amino$C_{1-6}$alkyl, or a radical of formula —Alk$^1$—C(=O)—R$^9$, —Alk$^1$—S(O)—R$^9$ or —Alk$^1$—S(O)$_2$—R$^9$; $R^2$ and $R^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy-$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl; or when on adjacent positions $R^2$ and $R^3$ taken together may form a bivalent radical; $R^4$ and $R^5$ each independently are hydrogen, $Ar^1$, $C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2$—$C_{1-6}$alkyl; $R^6$ and $R^7$ each independently are hydrogen, halo, cyano, $C_{1-6}$alkyl, $C_{1-6}$alkyloxy or $Ar^2$oxy; $R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxy-carbonyl$C_{1-6}$alkyl, hydroxycarbonyl$C_{1-6}$alkyl, hydroxy$C_{1-6}$alkyl, amino$C_{1-6}$alkyl, mono- or di($C_{1-6}$alkyl)amino$C_{1-6}$alkyl, halo$C_{1-6}$alkyl, $C_{1-6}$alkyloxy-$C_{1-6}$alkyl, aminocarbonyl$C_{1-6}$alkyl, $Ar^1$, $Ar^2C_{1-6}$alkyloxy$C_{1-6}$alkyl, $C_{1-6}$alkylthio$C_{1-6}$alkyl; $R^{10}$ is hydrogen, $C_{1-6}$alkyl or halo; $R^{11}$ is hydrogen or $C_{1-6}$alkyl; having farnesyl transferase inhibiting activity; their preparation, compositions containing them and their use as a medicine.

13 Claims, No Drawings

FARNESYL TRANSFERASE INHIBITING 2-QUINOLONE DERIVATIVES

CROSS REFERENCE TO RELATED APPLICATIONS

This application is a National Stage application under 35 U.S.C. 371 of PCT/EP96/04661 filed Oct. 25, 1996, which claims priority from EP95.202.945.2, filed Oct. 31, 1995.

The present invention is concerned with novel 2-quinolone derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzyme that catalyzes this modification, farnesyl protein transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated, oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

Unexpectedly, it has been found that the present novel compounds, all possessing a phenyl substituent on the 4-position of the 2-quinolone-moiety, show farnesyl transferase inhibiting activity.

The present invention encompasses compounds of formula (I)

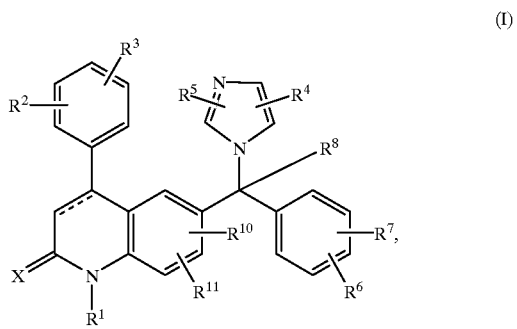

the pharmaceutically acceptable acid or base addition salts and the stereochemically isomeric forms thereof, wherein the dotted line represent an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —$Alk^1$—C(=O)—$R^9$, —$Alk^1$—S(O)—$R^9$ or —$Alk^1$—S(O)$_2$—$R^9$, wherein $Alk^1$ is $C_{1-6}$alkanediyl, $R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$ and $R^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl; or when on adjacent positions $R^2$ and $R^3$ taken together may form a bivalent radical of formula

| | |
|---|---|
| —O—CH$_2$—O— | (a-1), |
| —O—CH$_2$—CH$_2$—O— | (a-2), |
| —O—CH=CH— | (a-3), |
| —O—CH$_2$—CH$_2$— | (a-4), |
| —O—CH$_2$—CH$_2$—CH$_2$— | (a-5), or |
| —CH=CH—CH=CH— | (a-6); |

$R^4$ and $R^5$ each independently are hydrogen, $Ar^1$, $C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy or $Ar^2$oxy;

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, hydroxycarbonyl$C_{1-6}$alkyl, hydroxy$C_{1-6}$alkyl, amino$C_{1-6}$alkyl, mono- or di($C_{1-6}$alkyl)amino$C_{1-6}$alkyl, halo$C_{1-6}$alkyl, $C_{1-6}$alkyloxy$C_{1-6}$alkyl, aminocarbonyl$C_{1-6}$alkyl, $Ar^1$, $Ar^2C_{1-6}$alkyloxy$C_{1-6}$alkyl, $C_{1-6}$alkylthio$C_{1-6}$alkyl;

$R^{10}$ is hydrogen, $C_{1-6}$alkyl, $C_{1-6}$alkyloxy or halo;

$R^{11}$ is hydrogen or $C_{1-6}$alkyl;

$Ar^1$ is phenyl or phenyl substituted with $C_{1-6}$alkyl, hydroxy, amino, $C_{1-6}$alkyloxy or halo;

$Ar^2$ is phenyl or phenyl substituted with $C_{1-6}$alkyl, hydroxy, amino, $C_{1-6}$alkyloxy or halo.

As used in the foregoing definitions and hereinafter halo defines fluoro, chloro, bromo and iodo; $C_{1-6}$alkyl defines straight and branched chained saturated hydrocarbon radicals having from 1 to 6 carbon atoms such as, for example, methyl, ethyl, propyl, butyl, pentyl, hexyl and the like; $C_{1-8}$alkyl encompasses the straight and branched chained saturated hydrocarbon radicals as defined in $C_{1-6}$alkyl as well as the higher homologues thereof containing 7 or 8 carbon atoms such as, for example heptyl or octyl; $C_{1-12}$alkyl again encompasses $C_{1-8}$alkyl and the higher homologues thereof containing 9 to 12 carbon atoms, such as, for example, nonyl, decyl, undecyl, dodecyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "C(=O)" refers to a carbonyl group. The term "S(O)" refers to a sulfoxide and the term "S(O)$_2$" to a sulfon.

The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid or base addition salts and all stereoisomeric forms.

X is preferably oxygen.

$R^1$ is suitably hydrogen; $C_{1-6}$alkyl, preferably methyl, ethyl, propyl; $Ar^1$, preferably phenyl; $Ar^2C_{1-6}$alkyl, preferably benzyl, methoxyphenylethyl; a radical of formula —Alk—C(=O)—$R^9$, wherein Alk preferably is methylene, and $R^9$ preferably is hydroxy; $C_{1-6}$alkyloxy, e.g. ethoxy; $C_{1-8}$alkylamino substituted with $C_{1-6}$alkyloxycarbonyl.

$R^2$ and $R^3$ each independently are suitably hydrogen, halo, preferably fluoro, chloro, bromo; $C_{1-6}$alkyl, preferably methyl, trihalomethyl, preferably trifluoromethyl; $C_{1-6}$alkyloxy, preferably methoxy or ethoxy; $Ar^2$oxy, preferably phenoxy; $Ar^2C_{1-6}$alkyloxy, preferably benzyloxy; trihalomethoxy, preferably trifluoromethoxy.

$R^4$ and $R^5$ each independently are suitably hydrogen; $Ar^1$, preferably phenyl; $C_{1-6}$alkyl, preferably methyl; $C_{1-6}$alkylthio, preferably methylthio; amino; $C_{1-6}$alkyloxycarbonyl, preferably methoxycarbonyl.

$R^6$ and $R^7$ each independently are suitably hydrogen; halo, preferably chloro, fluoro; $C_{1-6}$alkyl, preferably methyl; $C_{1-6}$alkyloxy, preferably methoxy.

$R^8$ is suitably hydrogen; $C_{1-6}$alkyl, preferably methyl, ethyl or propyl; $Ar^1$, preferably chlorophenyl; $C_{1-6}$alkyl substituted with hydroxy (preferably hydroxymethylene), $C_{1-6}$alkyloxy (preferably methoxymethylene), amino, mono- or di-$C_{1-6}$alkylamino (preferably N,N-dimethylaminomethylene), $Ar^2C_{1-6}$alkyloxy (preferably chlorobenzyloxymethyl) or $C_{1-6}$alkylthio (methylthiomethylene).

$R^{10}$ and $R^{11}$ are hydrogen.

Preferably the substituent $R^{10}$ is situated on the 5 or 7 position of the quinolinone moiety and substituent $R^{11}$ is situated on the 8 position when $R^{10}$ is on the 7-position.

An interesting group of compounds are those compounds of formula (I) wherein $R^1$ is hydrogen, $C_{1-12}$alkyl or $C_{1-6}$alkyloxy$C_{1-6}$alkyl.

Another group of interesting compounds are those compounds wherein $R^3$ is hydrogen and $R^2$ is halo, preferably chloro, especially 3-chloro.

Still another group of interesting compounds are those compounds wherein $R^2$ and $R^3$ are on adjacent positions and form a bivalent radical of formula (a-1).

A further group of interesting compounds are those compounds wherein $R^5$ is hydrogen and $R^4$ is hydrogen, $C_{1-6}$alkyl or $Ar^1$, preferably phenyl.

Still another group of interesting compounds are those compounds of formula (I) wherein $R^7$ is hydrogen and $R^6$ is halo, preferably chloro, especially 4-chloro.

Particular compounds are those compounds of formula (I) wherein $R^8$ is hydrogen, $C_{1-6}$alkyl or hydroxy$C_{1-6}$alkyl.

More interesting compounds are those interesting compounds of formula (I), wherein $R^1$ is methyl, $R^2$ is 3-chloro, $R^4$ is hydrogen or 5-methyl, $R^5$ is hydrogen. $R^6$ is 4-chloro, and $R^8$ is hydrogen, $C_{1-6}$alkyl or hydroxy$C_{1-6}$alkyl.

Preferred compounds are 4-(3-chlorophenyl)-6-[(4-chlorophenyl)-1H-imidazol-1-ylmethyl]-1-methyl-2(1H)-quinolinone;

4-(3-chlorophenyl)-6-[(4-chlorophenyl)-1H-imidazol-1-ylmethyl]-2(1H)-quinolinone;

6-[1-(4-chlorophenyl)-2-hydroxy-1-(1H-imidazol-1-yl)ethyl]-1-methyl-4-phenyl-2(1H)-quinolinone;

4-(3-chlorophenyl)-6-[1-(4-chlorophenyl)-1-(1H-imidazol-1-yl)ethyl]-1-methyl-2(1H)-quinolinone;

4-(3-chlorophenyl)-6-[1-(4-chlorophenyl)-1-(5-methyl-1H-imidazol-1-yl)ethyl]-1-methyl-2(1H)-quinolinone;

4-(3-chlorophenyl)-6-[1-(4-chlorophenyl-2-hydroxy-1-(1H-imidazol-1-yl)ethyl]-1-methyl-2(1H)-quinolinone;

4-(3-chlorophenyl)-6-[(4-chlorophenyl)(1H-imidazol-1-yl)methyl]-1-(2-methoxyethyl)-2(1H)-quinolinone ethanedioate (2:3) monohydrate;

6-[(4-chlorophenyl)(1H-imidazol-1-yl)methyl]-4-(1,3-benzodioxol-5-yl)-1-methyl-2(1H)-quinolinone ethanedioate (1:1); the stereoisomeric forms and the pharmaceutically acceptable acid or base addition salts thereof.

The compounds of formula (I) can be prepared by N-alkylating an imidazole of formula (II) or an alkali metal salt thereof with a derivative of formula (III).

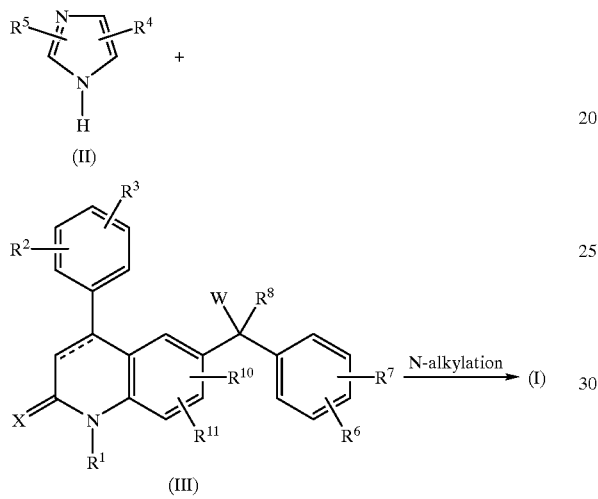

In formula (III) W represents an appropriate reactive leaving group such as, for example, halo, e.g., fluoro, chloro, bromo, iodo or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

The above described N-alkylation is conveniently carried out by stirring the reactants in the presence of a suitable solvent such as, for example, a polar aprotic solvent, e.g. N,N-dimethylformamide, N,N-dimethylacetamide, dimethyl sulfoxide, acetonitrile; preferably in the presence of an appropriate base such as, potassium carbonate, or an organic base, such as, for example, N,N-dimethyl-4-pyridinamine, pyridine, N,N-diethylethanamine. In some instances it may be advantageous to use an excess of imidazole (II) or to convert imidazole first into a suitable salt form thereof such as, for example, an alkali or earth alkaline metal salt, by reacting (II) with an appropriate base as defined hereinabove and subsequently using said salt form in the reaction with the alkylating reagent of formula (III).

The compounds of formula (I) may also be prepared by reacting an intermediate of formula (IV) with a reagent of formula (V), wherein Y is carbon or sulfur, such as, for example, a 1,1'-carbonyl-bis[1H-imidazole].

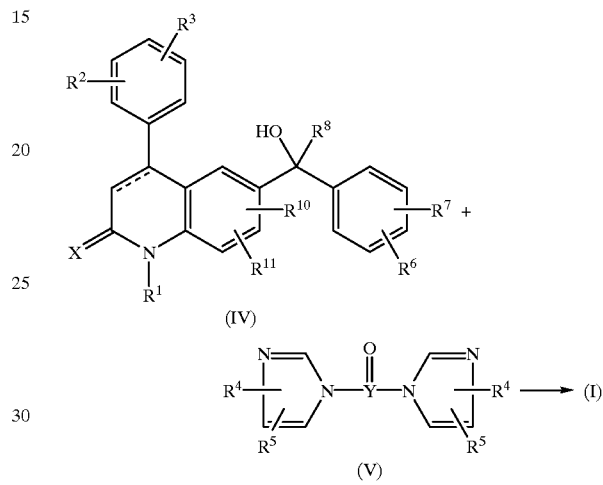

Said reaction may conveniently be conducted in a suitable solvent such as, for example, an ether, e.g., tetrahydrofuran; optionally in the presence of a base, such as sodium hydride.

In all of the foregoing and following preparations, the reaction products may be isolated from the reaction mixture and, if necessary, further purified according to methodologies generally known in the art such as, for example, extraction, distillation, crystallization, trituration and chromatography.

The compounds of formula (I) wherein the dotted line represents a bond, said compounds being defined as compounds of formula (I-a) may also be obtained by cyclizing an intermediate of formula (VI).

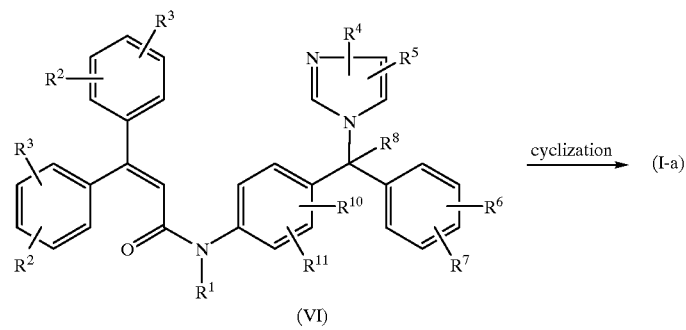

The cyclization reaction of (VI) may be conducted according to art-known cyclizing procedures as described in, for example, *Synthesis*, 739 (1975). Preferably the reaction is carried out in the presence of a suitable Lewis acid, e.g. aluminium chloride either neat or in a suitable solvent such as, for example, an aromatic hydrocarbon, e.g. chlorobenzene. Somewhat elevated temperatures may enhance the rate of the reaction. Also, depending on the nature of the substituents $R^2/R^3$, these substituents on one phenyl moiety may be different from the substituents $R^2/R^3$ on the other phenyl moiety, as described in Natarajan M. et al., *Indian Journal of Chemistry*, 23B:720–727 (1984).

Compounds of formula (I-a-1), wherein $R^1$ is hydrogen, X is oxygen and the dotted line represents a bond, can be prepared by hydrolysing intermediates of formula (XXVI), wherein R is $C_{1-6}$alkyl, according to art-known methods, such as stirring the intermediate (XXVI) in an aqueous acid solution. An appropriate acid is for instance hydrochloric acid. Subsequently, compounds of formula (I-a-1) may be converted to compounds of formula (I-a) by art-known N-alkylation methods.

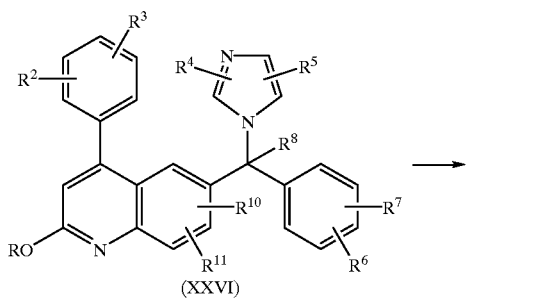

(XXVI)

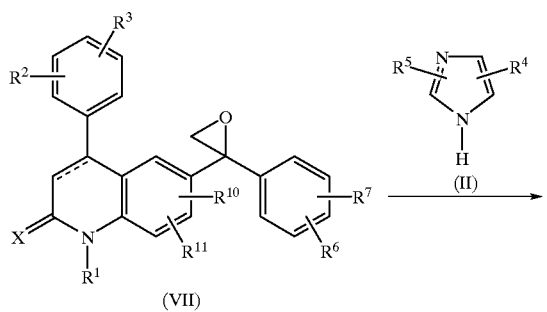

(I-a-1)

A compound of formula (I-b), defined as a compound of formula (I) wherein $R^8$ is hydroxymethylene, may be prepared by opening an epoxide of formula (VII) with an imidazole of formula (II).

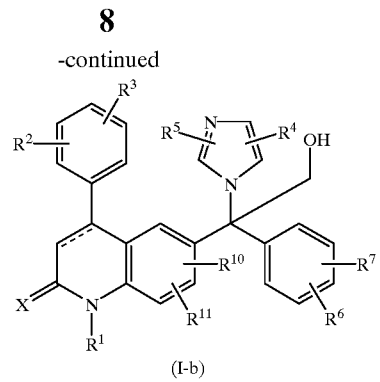

(I-b)

Compounds of formula (I), wherein $R^1$ is hydrogen and X is oxygen, said compounds being defined as compounds of formula (I-f-1) may be prepared by reacting a nitrone of formula (XV) with the anhydride of a carboxylic acid, such as, for example, acetic anhydride, thus forming the corresponding ester of the 2 position of the quinoline moiety. Said quinoline ester can be hydrolyzed in situ to the corresponding quinolinone using a base such as, for example, potassium carbonate.

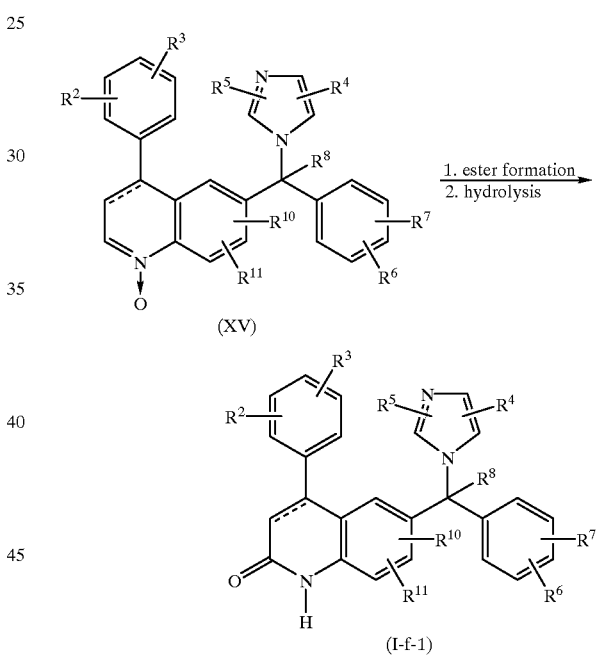

Alternatively, compounds of formula (I-f-1) can be prepared by reacting a nitrone of formula (XV) with a sulfonyl containing electrophilic reagent such as, for example, p-toluenesulfonylchloride in the presence of a base such as, for example, aqueous potassium carbonate. The reaction initially involves the formation of a 2-hydroxyquinoline derivative which is subsequently tautomerized to the desired quinolinone derivative. The application of art-known conditions of phase transfer catalysis may enhance the rate of the reaction.

Compounds of formula (I-f-1) may also be prepared by an intramolecular photochemical rearrangement of compounds of formula (XV). Said rearrangement can be carried out by dissolving the reagents in a reaction-inert solvent and irradiating at a wavelength of 366 nm. It is advantageous to use degassed solutions and to conduct the reaction under an inert atmosphere such as, for example, oxygen free argon or nitrogen gas, in order to minimize undesired side reactions or reduction of quantum yield.

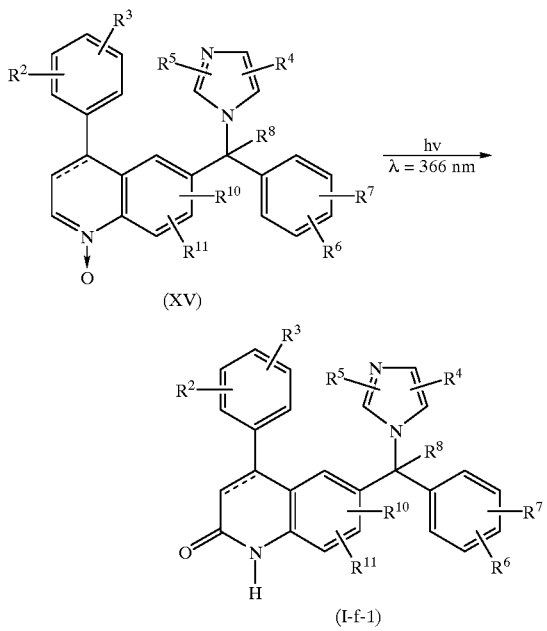

(XV)

(I-f-1)

Compounds of formula of formula (I), wherein $R^1$ is hydrogen, said components being defined as compounds of formula (I-c-1) may be converted into compounds of formula (I-c-2), wherein $R^{1b}$ is defined as $R^1$ except for hydrogen. For example, compounds of formula (I-c-1) may be N-alkylated with $R^{1b}$-$W^1$, wherein $W^1$ is a reactive leaving group such as, for example, halo or a sulfonyloxy group, in the presence of a base such as, for example, sodium hydride.

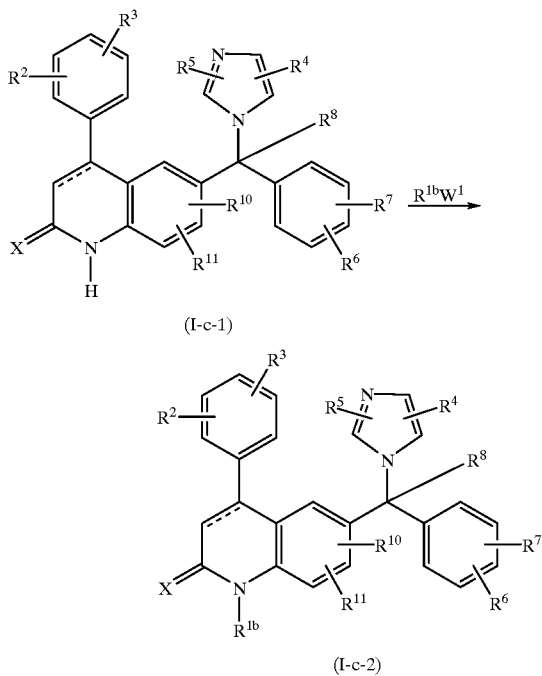

(I-c-1)

(I-c-2)

Said reaction may conveniently be carried out by mixing the reagents in a reaction-inert solvent such as, for example, N,N-dimethylformamide. It may be advisable to carry out the reaction at slightly lowered temperatures. Additionally, it may be advantageous to conduct said N-alkylation under an inert atmosphere such as, for example, argon or nitrogen gas. Said reaction may also be performed using art-known Phase Transfer Catalysis (PTC) conditions, such as stirring the reactants in a mixture of an aqueous concentrated sodium hydroxide solution and an organic solvent, such as tetrahydrofuran, in the presence of a phase transfer catalyst, such as benzyltriethylammoniumchloride (BTEAC).

In the case where $R^{1b}$ is aryl the N-alkylation may be performed by reacting a compound of formula (I-c-1) with a reactant like diphenyliodonium chloride in the presence of cuprous chloride (CuCl) in an appropriate solvent, e.g. methanol, in the presence of a base such as sodium methoxide.

Compounds of formula of formula (I), wherein $R^1$ is $R^{1b}$ and $R^8$ is hydrogen, said compounds being defined as compounds of formula (I-d-1) may also be converted into compounds of formula (I-d-2), wherein $R^{8a}$ is hydroxy$C_{1-6}$alkyl, $C_{1-6}$alkyl, $C_{1-6}$alkyloxy$C_{1-6}$alkyl, amino$C_{1-6}$alkyl, mono- or di-$C_{1-6}$alkylamino$C_{1-6}$alkyl. For example, compounds of formula (I-d-1) may be alkylated with a reagent of formula $R^{8a}$-$W^1$, wherein $W^1$ is a reactive leaving group such as for example, halo or a sulfonyloxy group, and in the presence of a base such as, for example, sodium hydride.

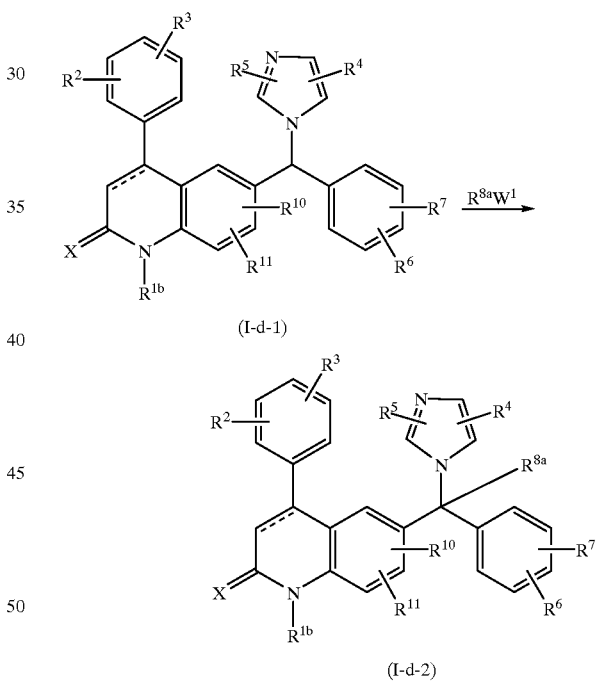

(I-d-1)

(I-d-2)

Said alkylation may conveniently be carried out by mixing the reagents in a reaction-inert solvent such as, for example, tetrahydrofuran or N,N-dimethylformamide, in the presence of a base such as potassium tert-butoxide. Additionally, it may be advantageous to conduct said alkylation under an inert atmosphere such as, for example, argon or nitrogen gas.

A compound of formula (I-e), defined as a compound of formula (I) wherein X is sulfur may be prepared by reacting the corresponding compound of formula (I-f), defined as a compound of formula (I), wherein X is oxygen, with a reagent like phosphorus pentasulfide or Lawesson's reagent ($C_{14}H_{14}O_2P_2S_4$).

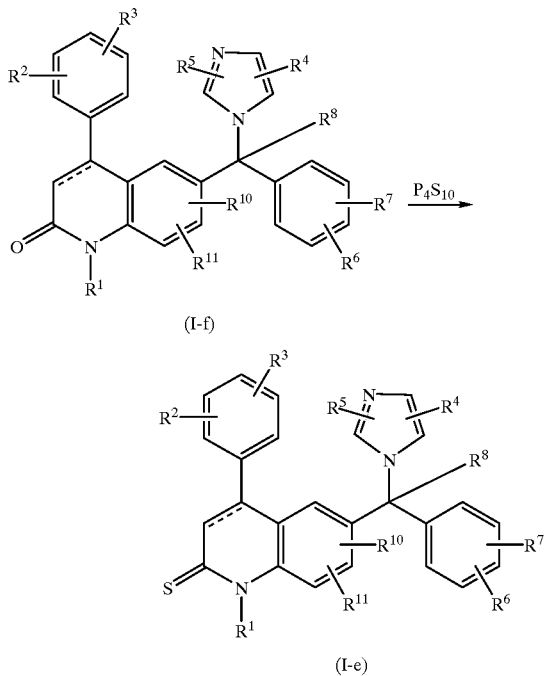

(I-f)

(I-e)

Said reaction may be performed by stirring and optionally heating a compound of formula (I-f) in the presence of phosphorus pentasulfide ($P_4S_{10}$) or Lawesson's reagent in a suitable solvent such as, for example, pyridine.

The compound of formula (I) may also be prepared by building up the imidazole ring as a final step. Such cyclization reactions are exemplified in example numbers 19 and 21.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

The intermediates described hereinabove can be prepared according to art-known methods. Some of these methods are shown hereinunder.

Intermediates of formula (IV) may be prepared by reacting a substituted 4-phenyl-2-quinolone derivative of formula (VIII) with a carboxylic acid of formula (IX) or a functional derivative thereof, e.g. an acid chloride, yielding a ketone of formula (X). Said reaction is performed by stirring the reactants in an appropriate solvent in the presence of an acid, such a polyphosphoric acid. Subsequently the ketone may be reduced yielding intermediates wherein $R^8$ is hydrogen or are reacted with an appropriate addition reagent.

Intermediates of formula (III) may be prepared starting from intermediates of formula (IV) by reacting an intermediate of formula (IV) with an appropriate reagent to convert the hydroxy group into an reactive leaving group. Appropriate conversion reagents are for example, thionyl chloride to obtain intermediates of formula (III) wherein W is chloro or chlorosulfite; or p-toluenesulfonylchloride to obtain intermediates of formula (III) wherein W is p-toluenesulfonyl group.

Intermediates of formula (VII) may be prepared by reacting a ketone of formula (X) with a sulfur ylide, e.g. dimethyloxosulfonium methylide, in appropriate conditions.

Scheme I

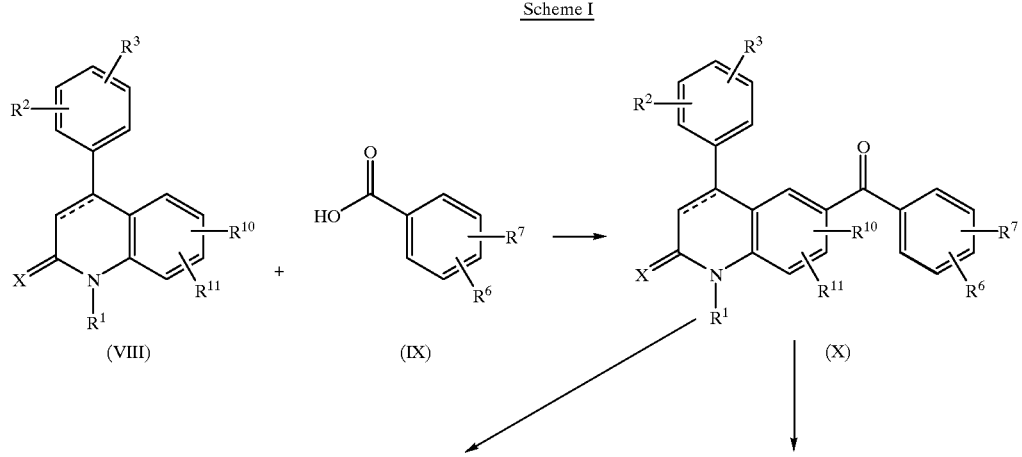

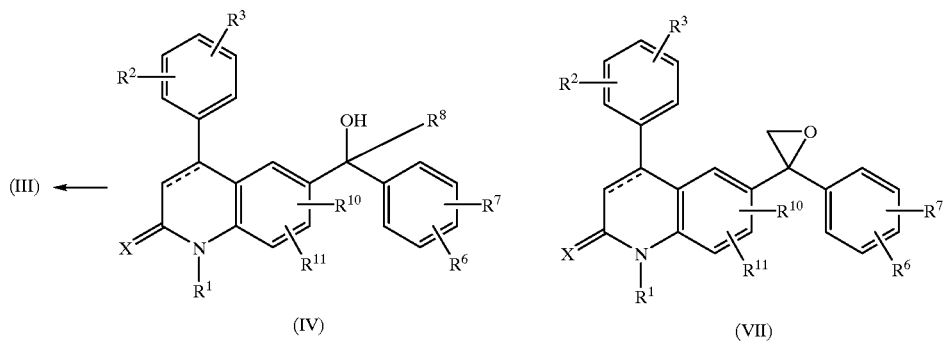

The intermediates of formula (VI) may be prepared as depicted below in scheme II. A nitrophenylderivative of formula (XI) is reacted with an imidazole of formula (II) in art-known conditions, yielding an intermediate of formula (XII). Said nitrophenyl derivative is subsequently reduced to give an aniline derivative of formula (XIII), which is then reacted with an acid derivative of formula (XIV) yielding an intermediate of formula (VI).

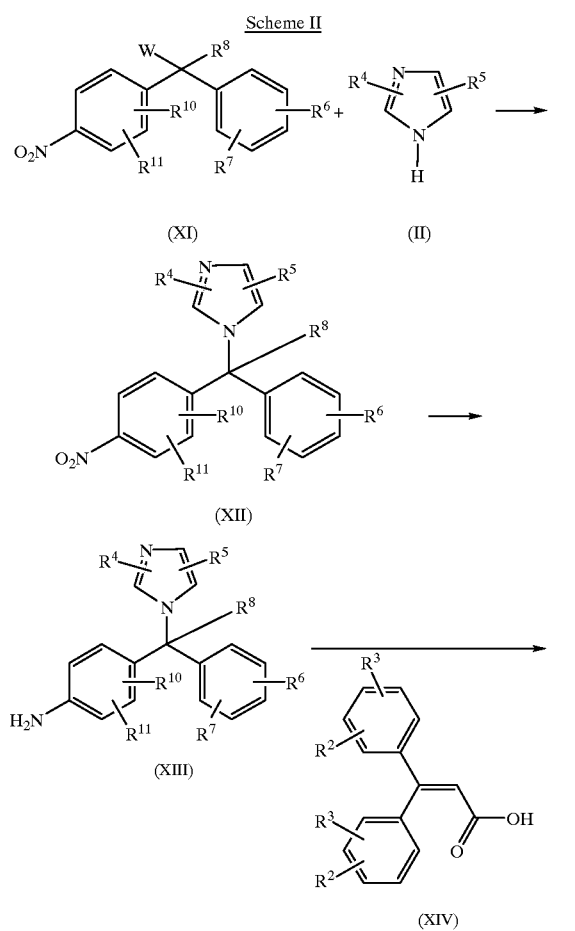

The intermediate nitrones of formula (XV) may be prepared by N-oxidizing quinoline derivatives of formula (XVI) with an appropriate oxidizing agent such as, for example, m-chloro-peroxybenzoic acid in an appropriate solvent such as, for example, dichloromethane. Quinolines of formula (XVI) may be prepared in analogy with the conversion of intermediates of formula (X) to intermediates of formula (III) and subsequent N-alkylation with intermediates of formula (II), but starting from quinoline derivatives prepared according to art-known procedures, e.g. as described in J. Kenner et al., *J. Chem. Soc.* 299 (1935). Said N-oxidation may also be carried out on a precursor of a quinoline of formula (XVI).

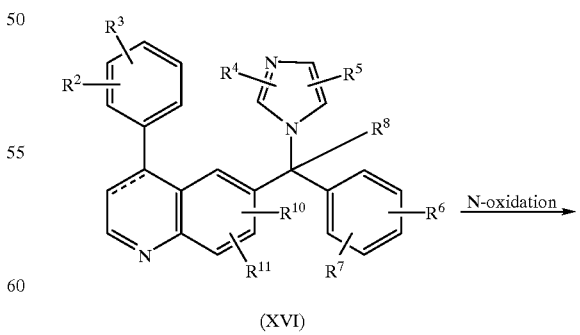

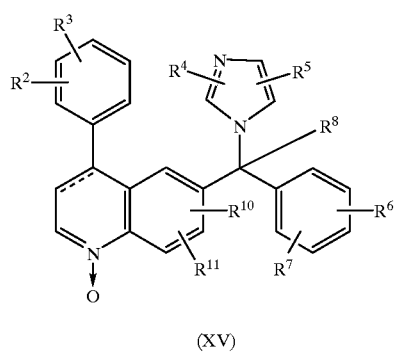

(XV)

The intermediates of formula (XVI) are supposed to be metabolized into compounds of formula (I). Hence, intermediates of formula (XVI) may act as prodrugs of compounds of formula (I).

The intermediates of formula (X-a), being intermediates of formula (X) wherein the dotted line is a bond, can be prepared according to scheme III.

Scheme III

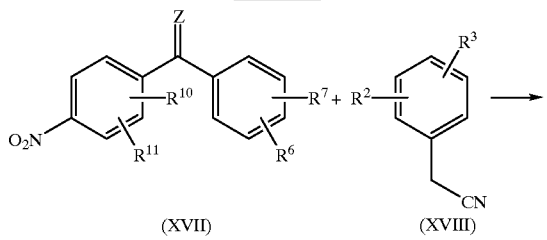

(XVII)  (XVIII)

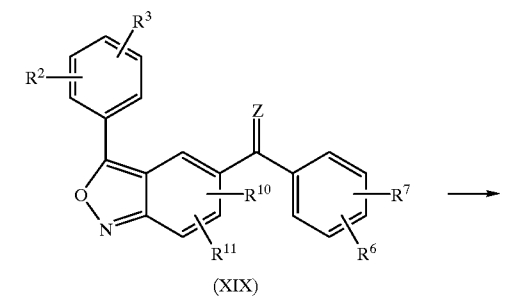

(XIX)

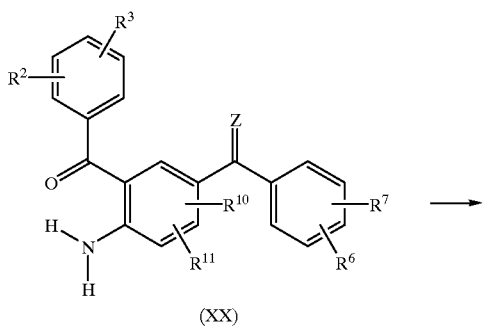

(XX)

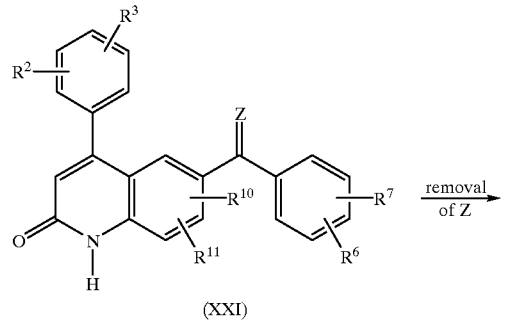

(XXI)

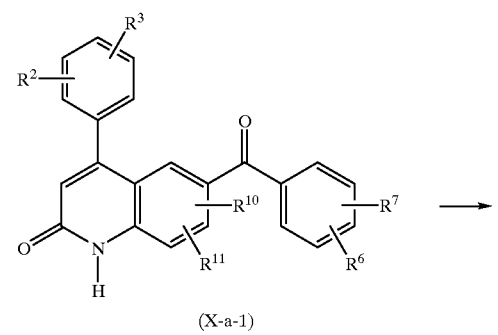

(X-a-1)

(X-a)

In scheme III, intermediates of formula (XVII) are reacted with intermediates of formula (XVIII), wherein Z is an appropriately protected oxo group such as, e.g. 1,3-dioxolane, yielding intermediates of formula (XIX), which are subsequently converted to intermediates of formula (XX) using catalytic hydrogenation conditions, e.g. by using hydrogen gas and palladium on carbon in a reaction-inert solvent such as, e.g. tetrahydrofuran. Intermediates of formula (XX) are converted to intermediates of formula (XXI) by submitting intermediates (XX) to an acetylation reaction, e.g. by treatment with the anhydride of carboxylic acid, e.g. acetic anhydride in a reaction-inert solvent, e.g. toluene, optionally in the presence of a base to capture the acid liberated during the reaction, and subsequent treatment with a base such as, e.g. potassium tert-butoxide in a reaction-inert solvent, e.g. 1,2-dimethoxyethane. Intermediates of formula (X-a-1), being intermediates of formula (X-a) wherein $R^1$ is hydrogen, can be obtained by removing the protecting group Z from intermediates of formula (XXI) using art-known reaction conditions, e.g. acidic conditions. Intermediates of formula (X-a-1) may be converted to intermediates of formula (X-a) using art-known N-alkylation reactions.

Also, intermediates of formula (X-a-1) can be obtained by treating intermediates of formula (XIX) with $TiCl_3$ in the presence of water, in a reaction-inert solvent, such as, e.g. tetrahydrofuran, or by catalytic hydrogenation, giving intermediates of formula (XXII) which are subsequently converted to intermediates (X-1) using the same reactions as described hereinabove for converting intermediates (XX) to intermediates (XXI).

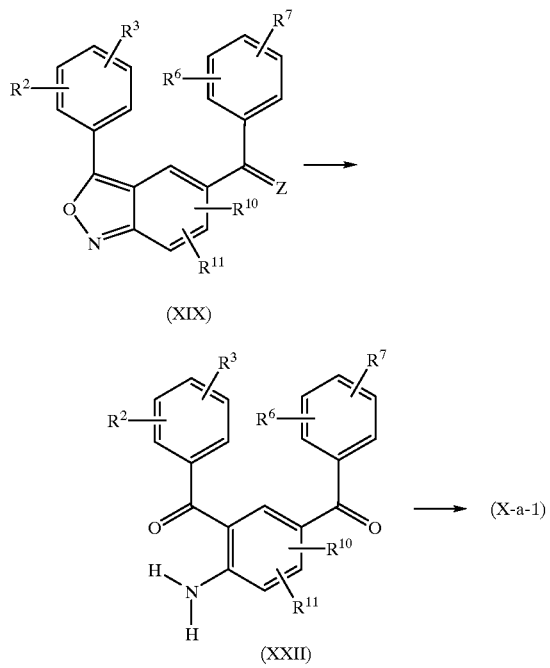

Scheme IV outlines the synthesis of intermediates of formula (XXVI-a), wherein $R^{8b}$ is a substituent appropriately selected from $R^8$ so as to be suitable in the addition reaction of the organolithium derivative of intermediate (XXIII) to the oxo group of intermediate (XXIV). $R^{8b}$ is for example hydrogen, $C_{1-6}$alkyl, $C_{1-6}$alkyloxycarbonyl and the like.

Scheme IV

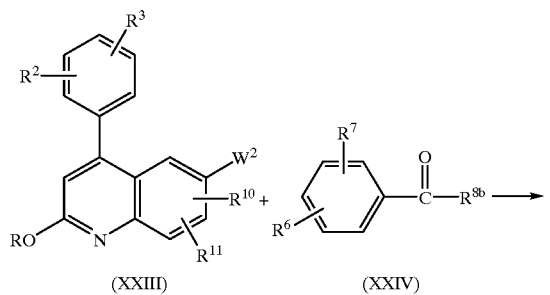

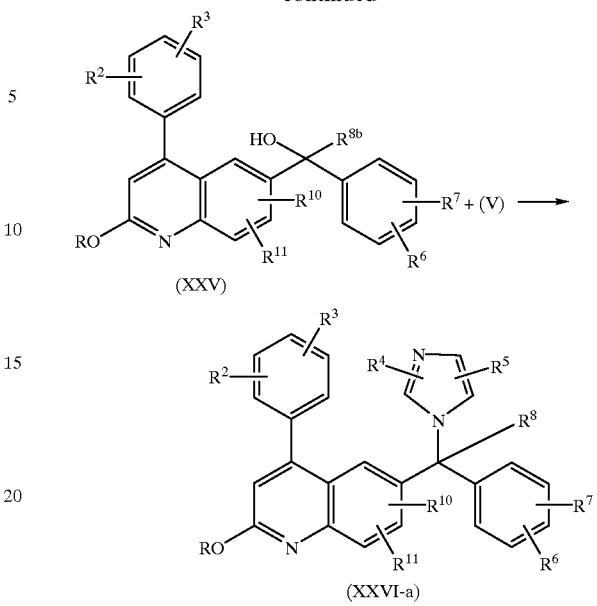

In scheme IV, an intermediate of formula (XXIII), wherein $W^2$ is halo, is treated with an organolithium reagent such as, e.g. n-butyllithium in a reaction-inert solvent, e.g. tetrahydrofuran, and subsequently reacted with an intermediate of formula (XXIV) giving an intermediate of formula (XXV), which is subsequently converted to an intermediate of formula (XXVI) by treatment with an intermediate of formula (V).

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

This invention provides a method for inhibiting the abnormal growth of cells, including transformed cells, by administering an effective amount of a compound of the invention.

Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of of tumors in vivo by a direct effect on tumor cell growth but also indirectly, i.e. by facilitating tumor-induced angiogenesis (Rak. J. et al, *Cancer Research,* 55, 4575–4580, 1995). Hence, pharmacologically targetting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes, i.e. the ras gene itself is not activated by mutation to an oncogenic mutation to an oncogenic form, with said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes may be inhibited by the compounds of this invention.

The present invention also relates to compounds of formula (I) as defined hereinabove for use as a medicine.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical composition are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

Experimental Part

Hereinafter "THF" means tetrahydrofuran, "DIPE" means diisopropylether, "DCM" means dichloromethane, "DMF" means N,N-dimethylformamide and "ACN" means acetonitrile. Of some compounds of formula (I) the absolute stereochemical configuration was not experimentally determined. In those cases the stereochemically isomeric form which was first isolated is designated as "A" and the second as "B", without further reference to the actual stereochemical configuration.

A. Preparation of the Intermediates

EXAMPLE 1 a) Imidazole (121.8 g) was added to a mixture of 1-(chlorophenylmethyl)-4-nitrobenzene (88.7 g) in ACN (1000 ml) and the reaction mixture was stirred and refluxed for 24 hours. The solvent was evaporated. The residue was dissolved in toluene, washed with a 10%

K₂CO₃ solution, dried (MgSO₄), filtered and evaporated. The residue was purified by column chromatography over silica gel (eluent: CH₂Cl₂/CH₃OH 98/2). The pure fractions were collected and the solvent was evaporated, yielding 53 g (53%) of 1-[(4-nitrophenyl)phenylmethyl]-1H-imidazole (interm. 1-a).

b) A mixture of intermediate (1-a) (39 g) in ethanol (300 ml) was hydrogenated (3.9 10⁵ Pa H₂) with Raney nickel (20 g) as a catalyst. After uptake of hydrogen (3 equivalents), the catalyst was filtered off and the filtrate was evaporated, yielding 34.6 g of (±)-4-[(1H-imidazol-1-yl)phenylmethyl]benzenamine (interm. 1-b).

c) A mixture of intermediate (1-b) (8.92 g) and 1-chloro-3,3-diphenyl-2-propen-1-one (10.42 g) in DCM (100 ml) was stirred at room temperature overnight. The mixture was poured into a 10% NaHCO₃-solution. This mixture was extracted with DCM and separated. The organic layer was dried (MgSO₄), filtered and evaporated, yielding 22.85 g (100%) of (±)-N-[4-[(1H-imidazol-1-yl)phenylmethyl]phenyl]-3,3-diphenyl-2-propenamide (interm. 1-c). The product was used without further purification.

EXAMPLE 2 a) 4-Chlorobenzoic acid (21.23 g) and 3,4-dihydro-4-phenyl-2(1H)-quinolinone (15 g) were heated in polyphosphoric acid (150 g) at 140° C. for 24 hours. The mixture was poured into ice water and filtered off. The precipitate was taken up in DCM. The organic layer was washed with NaHCO₃ (10%) and water, dried (MgSO₄) and evaporated. The residue was crystallized from 2-propanone, yielding 12.34 g (50%) of (±)-6-(4-chlorobenzoyl)-3,4-dihydro-4-phenyl-2(1H)-quinolinone; mp. 204° C. (interm. 2-a).

b) Sodium borohydride (12.5 g) was added portionwise at 0° C. to a solution of intermediate (2-a) (20 g) in methanol (200 ml) and THF (5 ml) and the mixture was stirred at room temperature for 2 hours. The mixture was quenched with water and evaporated. The residue was taken up in DCM and washed with K₂CO₃ (10%). The organic layer was dried (MgSO₄), filtered off and evaporated. The residue was purified by column chromatography over silica gel (eluent: CH₂Cl₂/CH₃OH 96/4). The pure fractions were collected and evaporated, yielding 2.8 g (14%) of (±)-6-[(4-chlorophenyl)hydroxymethyl]-3,4-dihydro-4-phenyl-2(1H)-quinolinone (interm. 2-b).

EXAMPLE 3

A mixture of (±)-6-[hydroxy(3-fluorophenyl)methyl]-4-phenyl-2(1H)-quinolinone (11 g) of thionyl chloride (11 ml) and DCM (120 ml) was stirred at room temperature for 12 hours. The solvent was evaporated till dryness and used without further purification, yielding 11.6 g (±)-6-[chloro(3-fluorophenyl)methyl]-4-phenyl-2(1H)-quinolinone (100%) (interm. 3).

EXAMPLE 4

A mixture of sodium hydride (1.75 g) in THF (30 ml) was stirred for 5 minutes. Tetrahydrofuran was removed by evaporation. Dimethyl sulfoxide (120 ml), then trimethylsulfoxonium iodide (12.2 g) were added and the resulting mixture was stirred for 30 minutes at room temperature, under N₂ flow. 6-(4-Chlorobenzoyl)-1-methyl-4-phenyl-2(1H)-quinolinone (17 g) was added portionwise and the reaction mixture was stirred for 2 hours at room temperature. Ethyl acetate and water were added. The organic layer was separated, washed twice with water, dried (MgSO₄), filtered and the solvent was evaporated. The crude product was used without further purification in next reaction step, yielding 17.6 g (100%) of (±)-6-[2-(4-chlorophenyl)-2-oxiranyl]-1-methyl-4-phenyl-2(1H)-quinolinone (interm. 4).

EXAMPLE 5 a) A mixture of 6-(4-chlorobenzoyl)-1-methyl-4-phenyl-2(1H)-quinolinone (24 g) in formamide (130 ml) and formic acid (100 ml) was stirred and heated at 160° C. for 12 hours. The mixture was poured into ice water and extracted with DCM. The organic layer was dried (MgSO₄), filtered off and evaporated till dryness. The product was used without further purification, yielding 24.2 g (93%) of (±)-N-[(4-chlorophenyl)-(1,2-dihydro-1-methyl-2-oxo-4-phenyl-6-quinolinyl)methyl]formamide (interm. 5-a).

b) A mixture of intermediate (5-a) (21.2 g) in hydrochloric acid (3 N) (150 ml) and 2-propanol (150 ml) was stirred and refluxed overnight. The mixture was poured into ice, basified with NH₄OH and extracted with DCM. The organic layer was dried (MgSO₄), filtered off and evaporated till dryness. The residue was purified by column chromatography over silica gel (eluent: CH₂Cl₂/CH₃OH/NH₄OH 98/2/0.1). The pure fractions were collected and evaporated, yielding 11.6 g (59%) of (±)-6-[amino-(4-chlorophenyl)methyl]-1-methyl-4-phenyl-2(1H)-quinolinone (interm. 5-b).

c) Ethyl N-cyano-methanimidate (3.6 g) was added dropwise at room temperature to a solution of intermediate (5-b) (10.6 g) in ethanol (90 ml) and the mixture was stirred at room temperature for 48 hours. Water and ethyl acetate were added, the organic layer was decanted, washed with water, dried (MgSO₄), filtered off and evaporated till dryness. The residue was purified by column chromatography over silica gel (eluent: CH₂Cl₂/CH₃OH/NH₄OH 97/3/0.1). The pure fractions were collected and evaporated, yielding 10.5 g (88%) of (±)-N-[[[(4-chlorophenyl)(1,2-dihydro-1-methyl-2-oxo-4-phenyl-6-quinolinyl)methyl]amino]methylene]cyanamide (interm. 5-c).

d) Ethyl 2-bromoacetate (2.45 ml) was added dropwise at 5° C. to a solution of intermediate (5-c) (9 g) and 2-methyl-2-propanol potassium salt (2.37 g) in dimethyl sulfoxide (100 ml) and the mixture was stirred at room temperature overnight. Water and ethyl acetate were added, the organic layer was decanted, dried (MgSO₄), filtered off and evaporated till dryness. The product was used without further purification, yielding (±)-ethyl N-[(4-chlorophenyl)(2,3-dihydro-1-methyl-2-oxo-4-phenyl-6-quinolinyl)-methyl]-N-[(cyanoimino)methyl]glycine (interm. 5-d).

EXAMPLE 6 a) isothiocyanato-1,1-dimethoxy-ethane (5.3 g) was added slowly to a solution of (±)-6-[amino(4-chlorophenyl)methyl]-4-phenyl-2(1H)-quinolinone (11 g) in methanol (100 ml) and the mixture was stirred and heated at 80° C. for 5 hours. The mixture was evaporated till dryness and the product was used without further purification, yielding 15.4 g (100%) of (±)-N-[(4-chlorophenyl)(1,2-dihydro-2-oxo-4-phenyl-6-quinolinyl)-methyl]-N'-(2,2-dimethoxyethyl)thiourea (interm. 6-a).

b) A mixture of intermediate (6-a) (15.3 g), iodomethane (2.27 ml) and potassium carbonate (5 g) in 2-propanone (50 ml) was stirred at room temperature for one night. The mixture was evaporated, the residue was taken up in DCM and washed with K₂CO₃ 10%. The organic layer was dried (MgSO₄), filtered off and evaporated, yielding 17.8 g (100%) of (±)-methyl N-[(4-chlorophenyl)(1,2-dihydro-2-oxo-4-phenyl-6-quinolinyl)-methyl]-N'-(2,2-dimethoxy-ethyl)carbamimidothioate (interm. 6-b), which was used without further purification.

EXAMPLE 7 a) Toluene (1900 ml) was stirred in a round-bottom flask (5 l) using a water separator. (4-chlorophenyl)(4-nitrophenyl)methanone (250 g) was added portionwise. p-Toluene-sulfonic acid (54.5 g) was added portionwise. Ethylene glycol (237.5 g) was poured out into the mixture. The mixture was stirred and refluxed for 48 hours. The solvent was evaporated. The residue was dissolved into ethyl acetate (5 l) and washed twice with a K₂CO₃ 10% solution. The organic layer was separated, dried (MgSO₄), filtered and the solvent was evaporated. The residue was stirred in DIPE, filtered off and dried (vacuum, 40° C., 24 hours), yielding 265 g (91%) of 2-(4-chlorophenyl)-2-(4-nitrophenyl-1,3-dioxolane (interm. 7-a).

b) Sodium hydroxide (16.4 g) and (3-methoxyphenyl) acetonitrile (20.6 ml) were added at room temperature to a solution of interm. (7-a) 25 g) in methanol (100 ml) and the mixture was stirred at room temperature overnight. Water was added, the precipitate was filtered off, washed with cold methanol and dried. The product was used without further purification, yielding 30 g (90%) of 5-[2-(4-chlorophenyl)-1,3-dioxolan-2-yl]-3-(3-methoxyphenyl)-2,1-benzisoxazole (interm. 7-b).

c) Interm (7-b) (30 g) of THF (250 ml) was hydrogenated with palladium on carbon (3 g) as a catalyst at room temperature for 12 hours under a 2.6 10⁵ Pa pressure in a Parr apparatus. After uptake of H₂ (1 equivalent), the catalyst was filtered through celite and the filtrate was evaporated till dryness. The product was used without further purification, yielding 31.2 g (100%) of (3-methoxyphenyl)[2-amino-5-[2-(4-chlorophenyl)-1,3-dioxolan-2-yl]phenyl]methanone (interm. 7-c).

d) Acetic anhydride (13.9 ml) was added to a solution of interm. (7-c) (31.2 g) in toluene (300 ml) and the mixture was stirred and refluxed for 2 hours. The mixture was evaporated till dryness and the product was used without further purification, yielding 36.4 g (100%) of N-[2-(3-methoxybenzoyl)-4-[2-(4-chlorophenyl)-1,3-dioxolan-2-yl]phenyl]acetamide (interm. 7-d).

e) Potassium tert-butoxide (33 g) was added portionwise at room temperature to a solution of interm. (7-d) (36.4 g) in 1,2-dimethoxyethane (350 ml) and the mixture was stirred at room temperature overnight. The mixture was hydrolized and extracted with DCM. The organic layer was dried (MgSO₄), filtered off and evaporated till dryness. The product was used without further purification, yielding 43 g (100) of 6-[2-(4-chlorophenyl)-1,3-dioxolan-2-yl]-4-(3-methoxyphenyl)-2(1H)-quinolinone (interm. 7-e).

f) A mixture of interm. (7-e) (43 g) in HCl (3N, 400 ml) and methanol 150 ml) was stirred and refluxed overnight. The mixture was cooled and filtered off. The precipitate was washed with water and diethyl ether and dried. The product was used without further purification, yielding 27 g (94%) of 6-(4-chlorobenzoyl)-4-(3-methoxyphenyl)-2 (1H)-quinolinone (interm. 7-f).

g) Methyl iodide (1.58 ml) was added to a solution of interm. (7-f) (7.6 g) and benzyltriethylammonium chloride (BTEAC) (2.23 g) in THF (80 ml) and sodium hydroxide (40%, 80 ml). The mixture was stirred at room temperature for 2 hours. Water was added and the mixture was extracted with ethyl acetate. The organic layer was dried (MgSO₄), filtered, and the solvent was evaporated. The residue was purified by flash column chromatography over silica gel (eluent: DCM 100%). The desired fractions were collected and the solvent was evaporated, yielding 7.1 g (90%) of 6-(4-chlorobenzoyl)-4-(3-methoxyphenyl)-1-methyl-2(1H)-quinolinone (interm. 7-g).

h) Interm. (b 7-g) (6.8 g) was added to DCM (210 ml), stirred at 0° C. Tribromoborane (67.3 ml) was added dropwise and the reaction mixture was stirred at 0° C. for 15 minutes. The mixture was brought to room temperature, stirred at room temperature for 30 minutes and K₂CO₃ 10% was added. The organic layer was separated, dried (MgSO₄), filtered, and the solvent was evaporated, yielding 6.6 g of 6-(4-chlorobenzoyl)-4-(3-hydroxyphenyl)-1-methyl-2(1H)-quinolinone (interm. 7-h) (quantitative yield; used in next reaction step, without further purification.

i) A mixture of interm. (7-h) (9.5 g), propyl iodide (5.9 ml) and K₂CO₃ (10.1 g) was stirred and refluxed for 4 hours. Water was added and the mixture was extracted with DCM. The organic layer was separated, dried (MgSO₄), filtered and the solvent was evaporated, yielding 10.4 g (100%) of 6-(4-chlorobenzoyl)-1-methyl-4-(3-propoxyphenyl)-2(1H)-quinolinone (interm. 7-i).

j) A solution of interm. (7-i) (3.55 g) in methanol (20 ml) and THF (20 ml) was cooled. Sodium borohydride (0.37 g) was added portionwise. The mixture was stirred at room temperature for 30 minutes, hydrolized and extracted with DCM. The organic layer was separated, dried (MgSO₄), filtered and the solvent was evaporated till dryness, yielding 3.5 g (100%) of (±)-6-[(4-chlorophenyl) hydroxymethyl]-1-methyl-4-(3-propoxyphenyl)-2(1H)-quinolinone (interm. 7-j).

k) A solution of interm. (8-a) (3.5 g) in thionyl chloride (30 ml) was stirred and refluxed overnight. The solvent was evaporated till dryness and the product was used without further purification, yielding 3.7 g (100%) of (±)-6-[chloro(4-chlorophenyl)methyl]-1-methyl-4-(3-propoxyphenyl)-2(1H)-quinolinone (interm. 7-k).

EXAMPLE 8 a) HCl/diethyl ether (30.8 ml) was added to a solution of 4-amino-4'-chlorobenzophenone (35 g) in ethanol (250 ml) at room temperature and the mixture was stirred for 15 minutes. FeCl₃.6H₂O (69.4 g) and then ZnCl₂ (2.05 g) were added portionwise and the mixture was stirred at 65° C. for 30 minutes. 3-Chloro-1-phenyl-1-propanone (25.46 g) was added and the mixture was stirred and refluxed for one night. The mixture was poured into ice and extracted with DCM. The organic layer was washed with K₂CO₃ 10%, dried (MgSO₄), filtered off and evaporated. The residue was crystallized from ACN. The mother layers were purified by column chromatography over silica gel (eluent: CH₂Cl₂/CH₃OH 99/1). The pure fractions were collected and evaporated, yielding 19.4 g (37%) of (4-chlorophenyl)(4-phenyl-6-quinolinyl)methanone (interm. 8-a).

b) Using the same reaction procedure as described in example 7j, intermediate (8-a) was converted to (±)-α-(4-chlorophenyl)-4-phenyl-6-quinolinemethanol (intermediate (8-b).

c) Using the same reaction procedure as described in example 7k, intermediate (8-b) was converted to (±)-6-

[chloro(4-chlorophenyl)methyl]-4-phenylquinoline hydrochloride (intermediate 8-c).

d) A mixture of interm. (8-c) (12.6 g) and 1H-imidazole (11.8 g) in ACN (300 ml) was stirred and refluxed for 16 hours. The mixture was evaporated till dryness and the residue was taken up in DCM. The organic layer was washed with $K_2CO_3$ 10%, dried ($MgSO_4$), filtered off and evaporated. The residue was purified by column chromatography over silica gel (eluent: $CH_2Cl_2/CH_3OH/NH_4OH$ 97.5/2.5/0.1). The pure fractions were collected and evaporated. The residue was converted into the nitric acid salt (1:2) and crystallized from $CH_3OH$/2-propanol/diethyl ether, yielding 4.28 g (28%) of (±)-6-[(4-chlorophenyl)-1H-imidazol-1-ylmethyl]-4-phenylquinoline dinitrate.monohydrate (interm. 8-d, mp. 152.° C.).

EXAMPLE 9 a) Interm. (7-a) (50 g) and then (3-chlorophenyl)acetonitrile (34.8 ml) were added to a mixture of sodium hydroxide (32.8 g) in methanol (100 ml). The mixture was stirred and refluxed till complete dissolution. The reaction was carried out twice with the same quantities. The mixtures were combined. Ice and then ethanol were added. The mixture was allowed to crystallize out. The precipitate was filtered off, washed with ethanol and dried, yielding 58 g (86%) of 3-(3-chlorophenyl)-5-[2-(4-chlorophenyl)-1,3-dioxolan-2-yl]-2,1-benzisoxazole (interm. 9-a).

b) $TiCl_3$/15% $H_2O$ (308 ml) was added at room temperature to a mixture of interm. (9-a) (51 g) in THF (308 ml). The mixture was stirred at room temperature for two days. Water was added and the mixture was extracted with DCM. The organic layer was separated, washed with $K_2CO_3$ 10%, dried ($MgSO_4$), filtered and the solvent was evaporated. Part of this fraction (5.9 g) was recrystallized from 2-propanone/$CH_3OH$/diethyl ether. The precipitate was filtered off and dried, yielding 1.92 g (41%) of 1-amino-2,4-phenylene-(3-chlorophenyl)(4-chlorophenyl)dimethanone (interm. 9-b).

c) Using the same reaction procedure as described in example 7d, intermediate (9-b) was converted to N-[2-(3-chlorobenzoyl)-4-(4-chlorobenzoyl)phenyl]acetamide (intermediate 9-c).

d) Using the same reaction procedure as described in example 7e, intermediate (9-c) was converted to 6-(4-chlorobenzoyl)-4-(3-chlorophenyl)-2(1H)-quinolinone (intermediate 9-d).

e) Sodium hydride (601 g) was added portionwise under $N_2$ flow to a solution of interm. (9-d) (15 g) in dimethyl sulfoxide (200 ml). The mixture was stirred at room temperature for 30 minutes. 2-Chloroethyl methyl ether (25.2 ml) was added. The mixture was stirred at 50° C. for 72 hours, poured out on ice and extracted with ethyl acetate. The organic layer was separated, washed with water, dried ($MgSO_4$), filtered and the solvent was evaporated. The residue was purified by column chromatography over silica gel (eluent: cyclohexane/ethyl acetate 70/30). The pure fractions were collected and the solvent was evaporated, yielding 6.2 g (36%) of 6-(4-chlorobenzoyl)-4-(3-chlorophenyl)-1-(2-methoxyethyl)-2(1H)-quinolinone (interm. 9-e).

f) Using the same reaction procedure as described in example 7j; intermediate (9-e) was converted to (±)-4-(3-chlorophenyl)-6-[(4-chlorophenyl)hydroxymethyl]-1-(2-methoxyethyl)-2(1H)-quinolinone (intermediate 9-f).

g) Using the same reaction procedure as described in example 7k, intermediate (9-f) was converted to (±)-6-[chloro(4-chlorophenyl)methyl]-4-(3-chlorophenyl)-1-(2-methoxyethyl)-2(1H)-quinolinone (intermediate 9-g).

EXAMPLE 10 a) n-Butyllithium (37.7 ml) was added slowly at −20° C. under $N_2$ flow to a mixture of 6-bromo-4-(3-chlorophenyl)-2-methoxyquinoline (20 g) in THF (150 ml). The mixture was stirred at −20° C. for 30 minutes and was then added slowly at −20° C. under $N_2$ flow to a mixture of ethyl 4-chloro-α-oxoobenzeneacetate (12.2 g) in THF (80 ml). The mixture was allowed to warm to room temperature and stirred at room temperature for 1 hour. Water was added and the mixture was extracted with ethyl acetate. The organic layer was separated, dried ($MgSO_4$), filtered and the solvent was evaporated. The residue (26.3 g) was purified by column chromatography over silica gel (eluent: $CH_2Cl_2$/cyclohexane 90/10). The pure fractions were collected and the solvent was evaporated, yielding 9.3 g (33.5%) of (±)-ethyl 4-(3-chlorophenyl)-α-(4-chlorophenyl)-α-hydroxy-2-methoxy-6-quinolineacetate (interm. 10-a).

b) Intermediate (10-a) (9.3 g) and 1,1'-carbonylbis-1H-imidazole (22 g) were heated at 120° C. for 1 hour. The mixture was cooled. Ice was added slowly and the mixture was extracted with DCM. The organic layer was separated, dried ($MgSO_4$), filtered and the solvent was evaporated. The residue (10.6 g) was purified by column chromatography over silica gel (eluent: $CH_2Cl_2$/2-propanol/$NH_4OH$ 95/5/0.5), yielding 7.15 g (±)-ethyl 4-(3-chlorophenyl)-α-(4-chlorophenyl)-α-(1H-imidazol-1-yl)-2-methoxy-6-quinolineacetate. (interm. 10-b).

B. Preparation of the Final Compounds

EXAMPLE 11

A mixture of intermediate (1-c) (22.85 g) and aluminium chloride (48 g) in chlorobenzene (200 ml) was heated at 95° C. overnight. The mixture was cooled, poured into ice water, basified with $NH_4OH$ and evaporated till dryness. The residue was taken up in DCM and ethanol. The residue was filtered and evaporated. The residue was taken up in DCM and stirred with HCl 3N overnight. The mixture was extracted, the aqueous layer was washed with ethyl acetate, basified with $NH_4OAc$ and then extracted with ethyl acetate and the organic layer was dried ($MgSO_4$) and evaporated. The residue was purified by column chromatography over silica gel (eluent: $CH_2Cl_2/CH_3OH/NH_4OH$ 95/5/0.05) (35–70 μm). The pure fractions were collected and evaporated, yielding 2.13 g (16%) of (±)-6-[(1H-imidazol-1-yl)phenylmethyl]-4-phenyl-2(1H)-quinolinone; mp. 253.0° C. (comp. 1).

EXAMPLE 12

Sodium hydride (0.002 g) and then 1,1'-carbonylbis-1H-imidazole (2.5 g) were added portionwise at room temperature to intermediate (2-b) (2.8 g) dissolved in THF (30 ml) and the mixture was stirred and heated at 60° C. for 1 hour. The mixture was hydrolysed with water and evaporated. The residue was taken up in DCM and washed with water. The organic layer was dried ($MgSO_4$), filtered off and evaporated. The residue was purified by column chromatography over silica gel (eluent:toluene/2-propanol/$NH_4OH$ 90/10/0.5). The pure fractions were collected and evaporated. The residue (2.1 g) was crystallized from 2-propanone, yielding 1.55 g (48%) of (±)-6-[(4-chlorophenyl)-1H-imidazol-1-ylmethyl]-3,4-dihydro-4-phenyl-2(1H)-quinolinone; mp. 225.0° C. (comp. 57).

EXAMPLE 13

A mixture of intermediate (3) (11.6 g), imidazole (6.5 g) and potassiumcarbonate (13.8 g) in ACN (150 ml) was refluxed for 12 hours. The mixture was evaporated till dryness, the residue was taken up in water and extracted with dichloromethane. The organic layer was dried (MgSO$_4$) and the residue was purified by column chromatography over silica gel (eluent: CH$_2$Cl$_2$/CH$_3$OH 95/5) (70–200 μm). The pure fractions were collected and evaporated yielding 9 g (71%) of (±)-6-[(3-fluorophenyl)(1H-imidazol-1-yl)methyl]-4-phenyl-2(1H)-quinolinone (comp. 5).

EXAMPLE 14

Sodium hydride (1.15 g) was added portionwise at 10° C. under N$_2$ to a mixture of compound (2) (10 g) in DMF (100 ml) and the mixture was stirred at room temperature for 30 minutes. Iodomethane (1.5 ml) was added dropwise at 15° C. and the mixture was stirred at room temperature for 1 hour. The mixture was poured into ice water and filtered off. The precipitate was taken up in a mixture of DCM and methanol. The organic layer was dried (MgSO$_4$), filtered off and evaporated. The residue was purified by column chromatography over silica gel (eluent:ethyl acetate/CH$_3$OH 95/5). The pure fractions were collected and evaporated. The residue (3.3 g) was recrystallized from CH$_3$CN/DIPE, yielding 1.9 g (19%) of (±)-6-[(4-chlorophenyl)-1H-imidazol-1-yl-methyl]-1-methyl-4-phenyl-2(1H)-quinolinone; mp. 154.7° C. (comp. 8).

EXAMPLE 15

A solution of sodium methoxide in methanol (2.8 ml) was added dropwise to a mixture of compound (2) (6 g) and diphenyliodonium chloride (6.9 g) in methanol (400 ml). Copper (I) chloride (1.72 g) was added and the mixture was stirred and heated at 60° C. for 12 hours. The mixture was filtered over celite and the filtrate was evaporated. The residue was taken up in DCM and NH$_4$OH 10%. The aqueous layer was extracted with DCM. The combined organic layers were washed with water, dried (MgSO$_4$), filtered off and evaporated in vacuo till dryness. The residue was purified by column chromatography over silica gel (eluent: CH$_2$Cl$_2$/CH$_3$OH/NH$_4$OH 98/2/0.1). The pure fractions were collected and evaporated. The residue (1.1 g) was dissolved in CH$_3$OH and converted into the nitric acid salt (1:1) in CH$_3$OH, yielding 0.9 g (11.2%) of (±)-6-[(4-chlorophenyl)-1H-imidazol-1-ylmethyl]-1,4-diphenyl-2(1H)-quinolinone mononitrate; mp. 212.4° C. (comp. 19).

EXAMPLE 16

2-Methyl-2-propanol, potassium salt (1.35 g) was added portionwise at 0° C. under N$_2$ to a mixture of compound (15) (2.8 g) and iodomethane (1.9 ml) in tetrahydrofuran (85 ml) and the mixture was stirred at room temperature for 5 minutes. The mixture was poured into ice water and extracted with ethyl acetate. The organic layer was dried (MgSO$_4$), filtered off and evaporated. The residue was purified by column chromatography over silica gel (eluent: CH$_2$Cl$_2$/CH$_3$OH/NH$_4$OH 97.5/2.5/0.1). The pure fractions were collected and evaporated. The residue (2.3 g) was recrystallized from CH$_3$OH and diethyl ether, yielding 1.7 g (60%) of (±)-4-(3-chlorophenyl)-6-[1-(4-chlorophenyl)-1-(1H-imidazol-1-yl)ethyl]-1-methyl-2(1H)-quinolinone; mp. 120.2° C. (comp. 62).

EXAMPLE 17

A mixture of intermediate (4) (17.6 g) and imidazole (9.3 g) in ACN (250 ml) was stirred and refluxed overnight, then cooled to room temperature. The precipitate was filtered off, washed with a 10% aqueous K$_2$CO$_3$ solution and diethyl ether, then air-dried, yielding 11.2 g (55%) of product. A sample (3 g) was recrystallized from THF, methanol, diethyl ether. The precipitate was filtered off and dried, yielding 2 g (37%) of (±)-6-[1-(4-chlorophenyl)-2-hydroxy-1-(1H-imidazol-1-yl)ethyl]-1-methyl-4-phenyl-2(1H)-quinolinone monohydrate, mp. 180° C. (comp. 59).

EXAMPLE 18

1-Chloro-4-chloromethylbenzene (3.2 g) was added to a solution of compound (59) (7 g) and benzyltriethylammonium chloride (1.75 g) in sodium hydroxide (40%) (100 ml) and THF (100 ml) and the mixture was stirred at room temperature overnight. Water and ethyl acetate were added. The organic layer was decanted, washed with water, dried (MgSO$_4$), filtered off and evaporated till dryness. The residue was purified by column chromatography over silica gel (eluent: CH$_2$Cl$_2$/CH$_3$OH/NH$_4$OH 98.5/1.5/0.1). The pure fractions were collected and evaporated. The residue (3.7 g) was recrystallized from 2-propanone/(C$_2$H$_5$)$_2$O, yielding 2.1 g (24%) of (±)-6-[1-(4-chlorophenyl)-2-[(4-chlorophenyl)methoxy]-1-(1H-imidazol-1-yl)ethyl]-1-methyl-4-phenyl-2(1H)-quinolinone; mp. 176.8° C. (comp. 61).

EXAMPLE 19

Sodium methoxide (0.8 ml) was added at room temperature to a solution of intermediate (5-d) in methanol (100 ml), the mixture was stirred at room temperature overnight and then stirred and refluxed for 2 hours. Water was added and the mixture was extracted with DCM. The organic layer was dried (MgSO$_4$), filtered off and evaporated till dryness. The residue was purified by column chromatography over silica gel (eluent: CH$_2$Cl$_2$/CH$_3$OH/NH$_4$OH 98/2/0.1). The pure fractions were collected and evaporated, yielding 8.3 g (79%) of product. A sample (2.3 g) was converted into the ethanedioic acid salt (2:3) and recrystallized from 2-propanone, yielding 2.35 g (63%) of (±)-methyl 4-amino-1-[(4-chlorophenyl)(1,2-dihydro-1-methyl-2-oxo-4-phenyl-6-quinolinyl)-methyl]-1H-imidazole-5-carboxylate ethanedioate (2:3); mp. 168.7° C. (comp. 70).

EXAMPLE 20

Nitric acid (30 ml) followed by sodium nitrite (0.64 g) were added at 0° C. to a solution of compound (70) (4.6 g) in phosphoric acid (45 ml) and the mixture was stirred at 0° C. for 45 minutes. Hypophosphorous acid (30 ml) was carefully added portionwise and the mixture was stirred at room temperature for 1 hour. The mixture was poured into ice, basified with NH$_4$OH and extracted with ethyl acetate. The organic layer was dried (MgSO$_4$), filtered off and evaporated till dryness. The residue was purified by column chromatography over silica gel (eluent: CH$_2$Cl$_2$/CH$_3$OH/NH$_4$OH 98.5/1.5/0.1). The pure fractions were collected and evaporated. The residue (1.5 g) was converted into the ethanedioic acid salt (2:3) and recrystallized from 2-propanone and DIPE, yielding 1.14 g (20%) of (±)-methyl 1-[(4-chlorophenyl)(1,2-dihydro-1-methyl-2-oxo-4-phenyl-6-quinolinyl)methyl]-1H-imidazol-5-carboxylate ethanedioate (2:3); mp. 140.8° C. (comp. 54).

EXAMPLE 21

Intermediate (6-b) (15.66 g) was added to sulfuric acid (120 ml) which was cooled till 0° C. and the mixture was stirred at room temperature for one night. The mixture was added carefully to a cooled solution at 0° C. of ice and concentrated $NH_4OH$. The basic aqueous layer was extracted with DCM. The organic layer was dried ($MgSO_4$), filtered off and evaporated till dryness. The residue was purified by column chromatography over silica gel (eluent: $CH_2Cl_2/CH_3OH/NH_4OH$ 97.5/2.5/0.2). The pure fractions were collected and evaporated, yielding 7.4 g (52%) of product. A sample was crystallized from 2-propanone, yielding 2 g of (±)-6-[(4-chlorophenyl)[2-methylthio)-1H-imidazol-1-yl]methyl]-4-phenyl-2(1H)-quinolinone monohydrate; mp. 205.6° C. (comp. 51).

EXAMPLE 22

A solution of compound (17) (12.7 g) in sodium hydroxide (3 N) (130 ml) was stirred at 120° C. overnight. The mixture was cooled to room temperature and $NH_4OH$ was added till pH=5.2. The precipitate was filtered off, washed with water and air-dried, yielding 12 g of (±)-6-[(4-chlorophenyl)-1H-imidazol-1-ylmethyl]-2-oxo-4-phenyl-1 (2H)-quinoline-1-acetic acid (comp. 38).

EXAMPLE 23

N,N'-methanetetrayl-biscyclohexanamine (5.3 g) in DCM was added dropwise at room temperature to a mixture of compound (38) (12.4 g) and methyl-2-amino-4-methyl-pentanoate (6 g) in THF (120 ml) and 1-hydroxybenzotriazolehydrate and the mixture was stirred at room temperature overnight. The mixture was poured into water and extracted with ethyl acetate. The organic layer was dried ($MgSO_4$), filtered off and evaporated. The residue was purified by column chromatography over silica gel (eluent: $CH_2Cl_2/CH_3OH/NH_4OH$ 97/3/0.1). The pure fractions were collected and evaporated, yielding 6.8 g (43%) of product. A sample was crystallized from DIPE, yielding 1 g of (±)-methyl 2-[[2-[6-[(4-chlorophenyl)-1H-imidazol-1-ylmethyl]-1,2-dihydro-2-oxo-4-phenyl-1-quinolinyl]-2-oxoethyl]amino]-4-methylpentanoate; mp. 117.9° C. (comp. 39).

EXAMPLE 24

Compound (2) (1 g) was dissolved in n-hexane (81 ml) and ethanol (54 ml). This solution was separated and purified by column chromatography over a Chiralcel AD column (250 g, 20 μm, Diacel; eluent: n-hexane/ethanol 60/40 vol %). Two desired fraction groups were collected. The fractions, corresponding to the first chromatographic peak, were evaporated. The residue was dissolved in small amounts of DCM. Diethyl ether was added until precipitation resulted. The precipitate was filtered off over a Millipore filter (10 μm), then dried (vacuum; 40° C. 2 hours), yielding 0.430 g (43). This fraction was dissolved in 2-propanone and precipitated with DIPE. The precipitate was filtered off and dried, yielding 0.25 g (25%) of (±)-(A)-6-[(4-chlorophenyl)-1H- imidazol-1-ylmethyl]-4-phenyl-2 (1H)-quinolinone; mp. 190.0° C.; $[\alpha]^{20}_D$=+13.10° (c=0.1% in methanol) (comp. 6). The fractions, corresponding to the second chromatographic peak, were evaporated. The residue was dissolved in small amounts of DCM. Diethyl ether was added until precipitation resulted. The precipitate was filtered off over a Millipore 10 μm filter, then dried (vacuum; 40° C.; 2 hours), yielding 0.410 g (41%). This fraction was dissolved in 2-propanone and precipitated with DIPE. The precipitate was filtered off and dried, yielding 0.20 g (20%) of (−)-(B)-6-[(4-chlorophenyl)-1H-imidazol-1-ylmethyl]-4-phenyl-2(1H)-quinolinone; mp. 155.8° C.; $[\alpha]^{20}_D$=−6.32° (c=0.1% in methanol) (comp. 7).

EXAMPLE 25

Phosphorous pentasulfide (4.45 g) was added portionwise at room temperature to a solution of (±)-4-(3-chlorophenyl)-6-[(4-chlorophenyl)-1H-imidazol-1-ylmethyl]-2(1H)-quinolinone (4.5 g) in pyridine (54 ml) and the mixture was stirred and refluxed for 4 hours. The mixture was evaporated till dryness and the residue was taken up in ethyl acetate. The organic layer was washed with HCl and water, dried ($MgSO_4$), filtered off and evaporated till dryness. The residue was purified by column chromatography over silica gel (eluent: $CH_2Cl_2/CH_3OH$ 97/3). The pure fractions were collected and evaporated. The residue (2.7 g) was crystallized from DMF, yielding 1.6 g (33%) of (±)-4-(3-chlorophenyl)-6-[(4-chlorophenyl)-1H-imidazol-1-yl-methyl]-2-(1H)-quinolinethione monohydrate; mp. 263.5° C. (comp. 72).

EXAMPLE 26

Imidazole (3.34 g) was added to a solution of interm. (8-b) (3.7 g) in ACN (50 ml). The mixture was stirred and refluxed for 4 hours. Water was added and he mixture was extracted with DCM. The organic layer was separated, dried ($MgSO_4$), filtered and the solvent was evaporated till dryness. The residue (3.8 g) was purified by column chromatography over silica gel (eluent: $CH_2Cl_2/CH_3OH$ 98/2). The pure fractions were collected and the solvent was evaporated. The residue was crystallized from 2-propanone/DIPE filtered off and dried, yielding 1.8 g (45%) of (±)-6-[(4-chlorophenyl)-1H-imidazol-1-ylmethyl]-1-methyl-4-(3-propoxyphenyl)-2(1H)-quinolinone ethanedioate (2:3) .sesquihydrate (comp. 74).

EXAMPLE 27

A mixture of intermediate (10-b) (7.1 g) in THF (25 ml) and HCl 3N (190 ml) was stirred at 120° C. for 2 hours. The mixture was poured out on ice, basified with $K_2CO_3$ and extracted with DCM. The organic layer was separated, dried ($MgSO_4$), filtered and the solvent was evaporated, yielding 6.2 g (90%) of (±)-ethyl 4-(3-chlorophenyl)-α-(4-chlorophenyl)-1,2-dihydro-α-(1H-imidazol-1-yl)-2-oxo-6-quinolineacetate (comp. 98).

TABLE 1

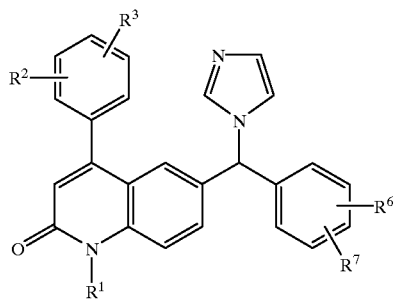

| Co. No. | Ex. No. | R¹ | R² | R³ | R⁶ | R⁷ | Physical data |
|---|---|---|---|---|---|---|---|
| 1 | 11 | H | H | H | H | H | mp. 255° C. |
| 2 | 11 | H | H | H | 4-Cl | H | mp. 260° C.(±) |
| 3 | 11 | H | H | H | 3-Cl | H | mp. 248° C. |
| 4 | 11 | H | H | H | 4-F | H | mp. 246.8° C. |
| 5 | 13 | H | H | H | 3-F | H | — |
| 6 | 24 | H | H | H | 4-Cl | H | (+)-(A) |
| 7 | 24 | H | H | H | 4-Cl | H | (−)-(B) |
| 8 | 14 | CH₃ | H | H | 4-Cl | H | mp. 160° C. |
| 9 | 14 | CH₂—CH₃ | H | H | 4-Cl | H | mp. 170° C. |
| 10 | 14 | benzyl | H | H | 4-Cl | H | mp. 180° C./.HNO₃.½ H₂O |
| 11 | 12 | H | 4-Cl | H | 4-Cl | H | mp. 170° C./.½ H₂O |
| 12 | 12 | H | 2-Cl | H | 4-Cl | H | mp. 244° C. |
| 13 | 12 | H | 3-Cl | H | 4-Cl | H | mp. 250° C. |
| 14 | 14 | (CH₂)₂—CH₃ | H | H | 4-Cl | H | mp. 170° C. |
| 15 | 13 | CH₃ | 3-Cl | H | 4-Cl | H | mp. 184° C. |
| 16 | 14 | (CH₂)₃—CH₃ | H | H | 4-Cl | H | mp. 118° C./.C₂H₂O₄.½ H₂O |
| 17 | 14 | CH₂COOC₂H₅ | H | H | 4-Cl | H | mp. 140° C. |
| 18 | 12 | H | 3-CH₃ | H | 4-Cl | H | — |
| 19 | 15 | phenyl | H | H | 4-Cl | H | mp. 215° C./.HNO₃ |
| 20 | 12 | H | 3-CF₃ | H | 4-Cl | H | mp. 244° C. |
| 21 | 12 | H | 3-F | H | 4-Cl | H | — |
| 22 | 24 | H | 3-Cl | H | 4-Cl | H | mp. 214° C./(A) |
| 23 | 24 | H | 3-Cl | H | 4-Cl | H | mp. 214° C./(B) |
| 24 | 12 | H | 3-OCH₃ | H | 4-Cl | H | mp. 174°/.½ H₂O |
| 25 | 12 | H | H | H | 4-CH₃ | H | mp. 230° C. |
| 26 | 12 | H | 3-Cl | 4-Cl | 4-Cl | H | mp. 260° C. |
| 27 | 12 | H | 4-CH₃ | H | 4-Cl | H | mp. 185° C. |
| 28 | 12 | H | 2-CH₃ | H | 4-Cl | H | mp. 234° C. |
| 29 | 14 | 4-methoxy-phenylethyl | H | H | 4-Cl | H | mp. 158° C. |
| 30 | 12 | H | 3-Br | H | 4-Cl | H | mp. > 260° C. |
| 31 | 12 | H | H | H | 2-Cl | 4-Cl | mp. 176° C. |
| 32 | 12 | H | H | H | 2-Cl | H | mp. 240° C. |
| 33 | 12 | H | H | H | 4-OCH₃ | H | mp. 210° C. |
| 34 | 12 | H | H | H | 3-Cl | 4-Cl | mp. 226° C. |
| 35 | 14 | CH₃ | 3-CH₃ | H | 4-Cl | H | mp. 162° C. |
| 36 | 14 | CH₃ | 3-OCH₃ | H | 4-Cl | H | mp. 260° C./.HNO₃.½ H₂O |
| 37 | 11 | H | 3-Cl | 5-Cl | 4-Cl | H | mp. 260° C. |
| 38 | 22 | CH₂—CO—OH | H | H | 4-Cl | H | — |
| 39 | 23 | CH₂—CO—NH—CH(COOCH₃)(CH₂—CH(CH₃)₂) | H | H | 4-Cl | H | — |
| 40 | 12 | H | 3-phenoxy | H | 4-Cl | H | mp. 230° C. |
| 41 | 12 | H | 3-benzyloxy | H | 4-Cl | H | mp. 154° C. |
| 42 | 12 | H | 3-ethoxy | H | 4-Cl | H | mp. 156° C. |
| 43 | 14 | CH₃ | 3-ethoxy | H | 4-Cl | H | mp. 142° C..½ C₂H₂O₄ |
| 44 | 14 | CH₃ | 3-benzyloxy | H | 4-Cl | H | mp. 136° C./.C₂H₂O₄ |
| 45 | 12 | H | 3-O—CF₃ | H | 4-Cl | H | mp. 255° C. |
| 74 | 26 | CH₃ | 3-propoxy | H | 4-Cl | H | .½ C₂H₂O₄.½ H₂O |
| 75 | 26 | CH₃ | 3-butoxy | H | 4-Cl | H | .½ C₂H₂O₄.H₂O |
| 76 | 26 | CH₃ | 3-O—CH(CH₃)₂ | H | 4-Cl | H | .½ C₂H₂O₄.2H₂O |
| 77 | 26 | CH₃OCH₂CH₂— | 3-Cl | H | 4-Cl | H | .½ C₂H₂O₄.H₂O |
| 78 | 26 | CH₃ | 2-ethoxy | H | 4-Cl | H | — |
| 79 | 26 | CH₃ | 3-OH | H | 4-Cl | H | — |

TABLE 1-continued

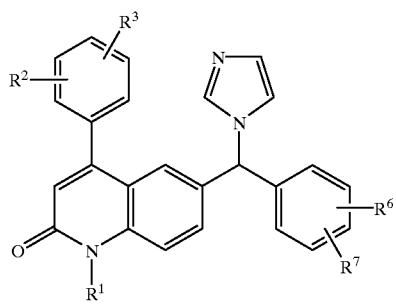

| Co. No. | Ex. No. | $R^1$ | $R^2$ | $R^3$ | $R^6$ | $R^7$ | Physical data |
|---|---|---|---|---|---|---|---|
| 80 | 26 | $(CH_3)_2N(CH_2)_2-$ | 3-Cl | H | 4-Cl | H | — |
| 81 | 26 | $CH_3$ | 3-$(CH_2)_2CH_3$ | H | 4-Cl | H | — |
| 84 | 26 | $CH_3$ | 3-CH=CH-$CH_3$ | H | 4-Cl | H | (E); |

TABLE 2

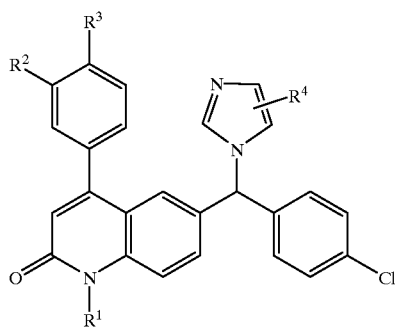

| Co. No. | Ex. No. | $R^1$ | $R^2$ | $R^3$ | $R^4$ | Physical data |
|---|---|---|---|---|---|---|
| 46 | 13 | H | H | H | 2-$CH_3$ | mp. > 260° C. |
| 47 | 13 | H | H | H | 4-phenyl | mp. 240° C. |
| 48 | 13 | H | H | H | 4-$CH_3$ | mp. 260° C. |
| 49 | 13 | H | H | H | 5-$CH_3$ | mp. > 260° C. |
| 50 | 13 | H | H | H | 2-phenyl | mp. 160° C. |
| 51 | 21 | H | H | H | 2-S-$CH_3$ | .$H_2O$ |
| 52 | 13 | H | Cl | H | 4-$CH_3$ | — |
| 53 | 11 | H | Cl | H | 5-$CH_3$ | — |
| 54 | 20 | $CH_3$ | H | H | 5-CO-$OCH_3$ | mp. 140° C./½ $C_2H_2O_4$ |
| 55 | 14 | $CH_3$ | Cl | H | 5-$CH_3$ | mp. 145° C./½ $C_2H_2O_4$ |
| 56 | 20 | $CH_3$ | Cl | H | 5-CO-$OCH_3$ | mp. 170° C./½ $C_2H_2O_4$ |
| 85 | 26 | $CH_3$ | Cl | H | 2-phenyl | — |
| 86 | 26 | $CH_3$ | Cl | H | 2-phenyl | .$C_2H_2O_4$ |
| 83 | 26 | $CH_3$ | —O—$CH_2$—O—* | H | .$C_2H_2O_4$ |

*$R^2$ and $R^3$ taken together to form a bivalent radical

TABLE 3

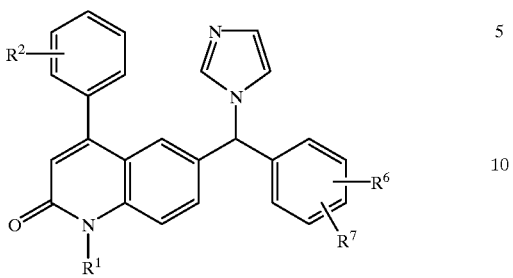

| Co. No. | Ex. No. | R¹ | R² | R⁶ | R⁷ | Physical data |
|---|---|---|---|---|---|---|
| 57 | 12 | H | H | 4-Cl | H | mp. 226° C. |

TABLE 4

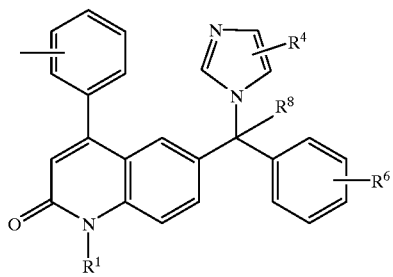

| Co. No. | Ex. No. | R¹ | R² | R⁴ | R⁶ | R⁸ | Physical data |
|---|---|---|---|---|---|---|---|
| 58 | 12 | H | H | H | 4-Cl | CH₃ | 255° C. |
| 59 | 17 | CH₃ | H | H | 4-Cl | CH₂—OH | mp. 160–170° C./.H₂O |
| 60 | 12 | H | H | H | 4-Cl | 4-chlorophenyl | >260° C./.½ H₂O |
| 61 | 18 | CH₃ | H | H | 4-Cl | 4-chlorobenzyl-oxymethyl | mp. 180° C. |
| 62 | 16 | CH₃ | 3-Cl | H | 4-Cl | CH₃ | mp. 125° C. |
| 63 | 16 | CH₃ | 3-Cl | H | 4-Cl | CH₂CH₃ | mp. 158° C./.C₂H₂O₄.H₂O |
| 64 | 16 | CH₃ | 3-Cl | 5-CH₃ | 4-Cl | CH₃ | mp. 170° C. |
| 65 | 16 | CH₃ | 3-Cl | H | 4-Cl | (CH₂)₂CH₃ | mp. 160° C./.HCl.H₂O |
| 66 | 17 | CH₃ | 3-Cl | H | 4-Cl | CH₂—OH | mp. 180° C. |
| 67 | 18 | CH₃ | 3-Cl | H | 4-Cl | CH₂—OCH₃ | mp. 178° C./.C₂H₂O₄ |
| 68 | 12 | CH₃ | 3-Cl | H | 4-Cl | CH₂—N(CH₃)₂ | mp. 96–110° C. |
| 69 | 12 | CH₃ | 3-Cl | H | 4-Cl | CH₂—S—CH₃ | mp. 120–150° C. .C₂H₂O₄.H₂O |
| 87 | 27 | H | 3-Cl | H | 4-Cl | —COOCH₂CH₃ | — |
| 88 | 14 | CH₃ | 3-Cl | H | 4-Cl | —COOCH₂CH₃ | — |

TABLE 5

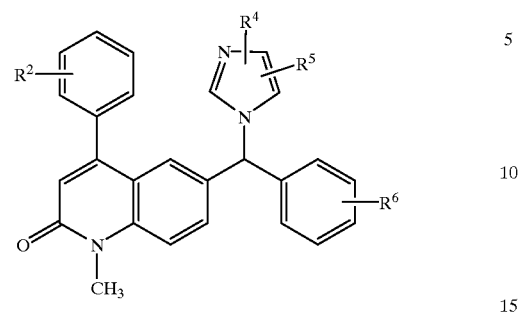

| Co. No. | Ex. No. | $R^2$ | $R^4$ | $R^5$ | $R^6$ | Physical data |
|---|---|---|---|---|---|---|
| 70 | 19 | H | 4-$NH_2$ | 5-$COOCH_3$ | 4-Cl | mp. 168.7° C./ ½ $C_2H_2O_4$ |
| 71 | 19 | 3-Cl | 4-$NH_2$ | 5-$COOCH_3$ | 4-Cl | — |

TABLE 6

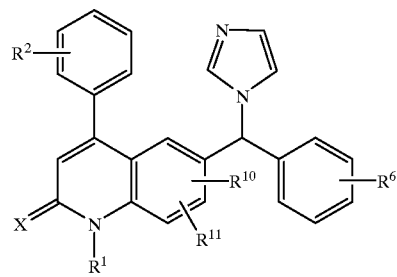

| Co. No. | Ex. No. | X | $R^1$ | $R^2$ | $R^6$ | $R^{10}$ | $R^{11}$ | Physical data |
|---|---|---|---|---|---|---|---|---|
| 72 | 25 | S | H | 3-Cl | 4-Cl | H | H | mp. 263.5° C./$H_2O$ |
| 73 | 25 | S | $CH_3$ | 3-Cl | 4-Cl | H | H | mp. 161.1° C./½ $H_2O$ |
| 89 | 26 | O | $CH_3$ | 3-Cl | 4-Cl | H | 8-$CH_3$ | — |
| 82 |    | O | H | 3-Cl | 4-Cl | 7-$CH_3$ | 8-$CH_3$ | mp. 161° C. |

C. Pharmacological example

EXAMPLE 28

In Vitro Assay for Inhibition of Farnesyl Protein Transferase

Human farnesyl protein transferase was prepared essentially as described (Y. Reiss et al., Methods: A Companion to Methods in Enzymology vol 1, 241–245, 1990). Kirsten virus transformed human osteosarcoma (KHOS) cells (American Type Culture Collection, Rockvill, Md., USA) grown as solid tumors in nude mice or grown as monolayer cell cultures were used as a source of human enzyme. Briefly, cells or tumors were homogenized in buffer containing 50 mM Tris, 1 mM EDTA, 1 mM EGTA and 0.2 mM phenylmethylsulfonylfluoride (pH 7.5). The homogenates were centrifuged 28,000× g for 60 min and the supernatants collected. A 30–50% ammonium sulfate fractin was prepared, and the resulting precipitate was resuspended in a small (10 to 20 ml) volume of dialysis buffer containing 20 mM Tris, 1 mM dithiothreitol and 20 $\mu$M $ZnCl_2$. The ammonium sulfate fraction was dialyzed overnight against two changes of the same buffer. The dialyzed material was applied to a 10×1 cm Q Fast Flow Sepharose (Pharmacia LKB Biotechnology Inc., Piscataway, N.J., USA) which had been preequilibrated with 100 ml of dialysis buffer supplemented with 0.05M NaCl. The column was washed with an additional 50 ml of dialysis buffer plus 0.05M NaCl followed by a gradient from 0.05M to 0.25M NaCl prepared in dialysis buffer. The enzyme activity was eluted with a linear gradient of 0.25 to 1.0M NaCl prepared in the dialysis buffer. Fractions containing 4 to 5 ml volumes of column eluate were collected and analyzed for farnesyl protein transferase activity. Fractions with enzyme activity were pooled and supplemented with 100 $\mu$M $ZnCl_2$. Enzyme samples were stored frozen at −70° C. The activity of farnesyl protein transferase was measured using the Farnesyl Transferase [$^3$H] Scintillation Proximity Assay (Amersham International plc., England) under the conditions specified by the manufacturer. To assay for inhibitors of the enzyme, 0.20 $\mu$Ci of the [$^3$H]-farnesylpyrophosphate substrate and the biotinylated lamin B peptide substrate (biotin-YRASNRSCAIM) were mixed with test compounds in a reaction buffer consisting of 50 mM HEPES, 30 mM $MgCl_2$, 20 mM KCl, 5 mM dithiothreitol, 0.01% Triton X-100. Test compounds were delivered in a 10 µl volume of dimethylsulfoxide (DMSO) to achieve concentrations of 1 and 10 µg/ml in a final volume of 100 µl. The reaction mixture was warmed to 37° C. The enzyme reaction was started by adding 20 µl of diluted human farnesyl protein transferase. Sufficient enzyme preparation was added to produce between 4000 to 15000 cpm of reaction product during the 60 min of reaction incubation at 37° C. Reactions were terminated by the addition of STOP/scintillation proximity bead reagent (Amersham). The reaction product [$^3$H]-farnesyl-(Cys)-biotin lamin B peptide was captured on the streptavidin linked scintillation proximity bead. The amount of [$^3$H]-farnesyl-(Cys)-biotin lamin B peptide synthesized in the presence or absence of test compounds was quantified as cpm by counting on a Wallac Model 1480 Microbeta Liquid Scintillation Counter. The cpm of product was considered to be farnesyl protein transferase activity. The protein farnesyl transferase activity observed in the presence of test compound was normalized to farnesyl transferase activity in the presence of 10% DMSO and expressed as per cent inhibition. In separate studies, some test compounds exhibiting 50% or greater inhibition of farnesyl protein transferase activity were evaluated for concentration-dependent inhibition of enzyme activity. The effects of test compounds in these studies were calculated as $IC_{50}$ (concentration of test compound producing 50% inhibition of enzyme activity) using the LGIC50 computer program written by the Science Information Division of R. W. Johnson Pharmaceutical Research Institue (Spring House, Pa., USA) on a VAX computer.

TABLE 7

| Co. No. | $IC_{50}$ (µM) |
| --- | --- |
| 1 | 0.93 |
| 2 | 0.18 |
| 3 | 1.4 |
| 4 | 0.315 |
| 7 | 0.11 |
| 8 | 0.07 |
| 10 | 0.22 |
| 11 | 0.32 |
| 12 | 3.2 |
| 13 | 0.034 |
| 14 | 0.7 |
| 15 | 0.016 |
| 17 | 0.23 |
| 18 | 0.04 |
| 20 | 0.24 |
| 21 | 0.15 |
| 23 | 0.015 |
| 24 | 0.032 |
| 25 | 0.262 |
| 26 | 0.227 |
| 27 | 0.193 |
| 28 | 2.2 |
| 29 | 2.4 |
| 30 | 0.021 |
| 31 | 0.48 |
| 32 | 0.53 |
| 33 | 0.85 |
| 34 | 0.6 |
| 37 | 0.096 |
| 39 | 0.047 |

TABLE 7-continued

| Co. No. | $IC_{50}$ (µM) |
| --- | --- |
| 47 | 0.105 |
| 49 | 0.3 |
| 53 | 0.032 |
| 57 | 1.2 |
| 58 | 0.27 |
| 59 | 0.013 |
| 62 | 0.022 |
| 63 | 0.03 |
| 64 | 0.011 |
| 65 | 0.051 |
| 66 | 0.0056 |
| 77 | 0.0072 |
| 83 | 0.0034 |

EXAMPLE 29

"Ras-Transformed Cell Phenotype Reversion Assay"

Insertion of activated oncogenes such as the mutant ras gene into mouse NIH 3T3 cells converts the cells to a transformed phenotype. The cells become tumorigenic, display anchorage independent growth in semi-solid medium and lose contact inhibition. Loss of contact inhibition produces cell cultures which no longer form uniform monolayers. Rather, the cells pile up into multicellular nodules and grow to very high saturation densities in plastic tissue culture dishes. Agents such as protein farnesyl transferase inhibitors which revert the ras transformed phenotype restore the uniform monolayer growth pattern to cells in culture. This reversion is easily monitored by counting the number of cells in tissue culture plates. Transformed cells will achieve higher cell numbers than cells which have reverted to an untransformed phenotype. Compounds which revert the transformed phenotype should produce antitumor effects in tumors bearing ras gene mutations.

Method

Compounds are screened in tissue culture in NIH 3T3 cells transformed by the T24 activated human H-ras gene. Cells are seeded at an initial density of 200,000 cells per well (9.6 $cm^2$ surface area) in six-well cluster tissue culture plates. Test compounds are immediately added to 3.0 ml cell growth mediuim in a 3.0 µl volume of DMSO, with a final concentration of DMSO in the cell growth medium of 0.1%. The test compounds are run at concentrations of 5, 10, 50, 100, and 500 nM along with a DMSO treated vehicle control. (In case a high activity is observed at 5 nM, the test compound is tested at even lower concentrations.) The cells are allowed to proliferate for 72 hours. Then the cells are detached in 1.0 ml trypsin-EDTA cell dissociation medium and counted on a Coulter particle counter.

Measurements

Cell numbers expressed as cells per well are measured using a Coulter Particle Counter.

All cell counts were corrected for the initial cell input density by subtracting 200,000.

Control cell counts=[cell counts from cells incubated with DMSO vehicle—200,000]

Test compound cell counts=[cell counts from cells incubated with test compound—200,000].

$$\text{Test compound \% inhibition} = \left[1 - \frac{\text{test compound cell counts}}{\text{control cell counts}}\right] \times 100\%.$$

$IC_{50}$ (i.e. the test compound concentration required to inhibit enzyme activity by 50%) is calculated if sufficient data are available, summarized in table 8.

TABLE 8

| Co. No. | $IC_{50}$ (nM) |
|---|---|
| 23 | 204 |
| 63 | 294 |
| 64 | 133 |
| 66 | 53 |
| 67 | 114 |
| 69 | 500 |
| 74 | 500 |
| 77 | 189 |
| 80 | 169 |
| 83 | 68 |
| 89 | 445 |

D. Composition examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid or base addition salt or a sterochemically isomeric form thereof.

EXAMPLE 30

Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 31

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 32

Film-coated tables

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denatured ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

EXAMPLE 33

Injectable solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

EXAMPLE 34

Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into moulds at a temperature of 37–38° C. to form 100 suppositories each containing 30 mg/ml of the A.I.

We claim:

1. A compound of formula (I), (I)

a steroisomeric form thereof, a pharmaceutically acceptable acid or base addition salt thereof; wherein the dotted line represents an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —Alk$^1$—C(=O)—R$^9$, —Alk$^1$—S(O)—R$^9$ or —Alk$^1$—S(O)$_2$—R$^9$, wherein Alk$^1$ is $C_{1-6}$alkanediyl;

$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$ and $R^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, aminoC$_{1-6}$alkyloxy, mono- or di(C$_{1-6}$alkyl) aminoC$_{1-6}$alkyloxy, Ar$^1$, Ar$^2$C$_{1-6}$alkyl, Ar$^2$oxy, Ar$^2$C$_{1-6}$alkyloxy, hydroxycarbonyl, C$_{1-6}$alkyloxycarbonyl, trihalomethyl, trihalomethoxy, C$_{2-6}$alkenyl; or when on adjacent positions R$^2$ and R$^3$ taken together may form a bivalent radical of formula —O—CH$_2$—O— (a-1), —O—CH$_2$—CH$_2$—O— (a-2), —O—CH=CH— (a-3), —O—CH$_2$—CH$_2$— (a-4), —O—CH$_2$—CH$_2$—CH$_2$— (a-5), or —CH=CH—CH=CH— (a-6);

R$^4$ and R$^5$ each independently are hydrogen, Ar$^1$, C$_{1-6}$alkyl, C$_{1-6}$alkyloxyC$_{1-6}$alkyl, C$_{1-6}$alkyloxy, C$_{1-6}$alkylthio, amino, hydroxycarbonyl, C$_{1-6}$alkyloxycarbonyl, C$_{1-6}$alkylS(O)C$_{1-6}$alkyl or C$_{1-6}$alkylS(O)$_2$C$_{1-6}$alkyl;

R$^6$ and R$^7$ each independently are hydrogen, halo, cyano, C$_{1-6}$alkyl, C$_{1-6}$alkyloxy or Ar$^2$oxy;

R$^8$ is hydrogen, C$_{1-6}$alkyl, cyano, hydroxycarbonyl, C$_{1-6}$alkyloxycarbonyl, C$_{1-6}$alkylcarbonylC$_{1-6}$alkyl, cyanoC$_{1-6}$alkyl, C$_{1-6}$alkyloxycarbonylC$_{1-6}$alkyl, hydroxycarbonylC$_{1-6}$alkyl, hydroxyC$_{1-6}$alkyl, aminoC$_{1-6}$alkyl, mono- or di(C$_{1-6}$alkyl) aminoC$_{1-6}$alkyl, haloC$_{1-6}$alkyl, C$_{1-6}$alkyloxyC$_{1-6}$alkyl, aminocarbonylC$_{1-6}$alkyl, Ar$^1$, Ar$^2$C$_{1-6}$alkyloxyC$_{1-6}$alkyl, C$_{1-6}$alkylthioC$_{1-6}$alkyl;

R$^{10}$ is hydrogen, C$_{1-6}$alkyl, C$_{1-6}$alkyloxy or halo;

R$^{11}$ is hydrogen or C$_{1-6}$alkyl;

Ar$^1$ is phenyl or phenyl substituted with C$_{1-6}$alkyl, hydroxy, amino, C$_{1-6}$alkyloxy or halo; and Ar$^2$ is phenyl or phenyl substituted with C$_{1-6}$alkyl, hydroxy, amino, C$_{1-6}$alkyloxy or halo.

2. A compound as claimed in claim 1 wherein X is oxygen.

3. A compound as claimed in claim 1 wherein R$^1$ is hydrogen, C$_{1-6}$alkyl or C$_{1-6}$alkyloxyC$_{1-6}$alkyl.

4. A compound as claimed in claim 1 wherein R$^6$ is hydrogen and R$^7$ is halo.

5. A compound as claimed in claim 1 wherein R$^8$ is hydrogen, C$_{1-6}$alkyl or hydroxy-C$_{1-6}$alkyl.

6. A compound as claimed in claim 1 wherein the compound is 4-(3-chlorophenyl)-6-[(4-chlorophenyl)-1H-imidazol-1-ylmethyl]-1-methyl-2(1H)-quinolinone;

4-(3-chlorophenyl)-6-[(4-chlorophenyl)-1H-imidazol-1-ylmethyl]-2(1H)-quinolinone;

6-[1-(4-chlorophenyl)-2-hydroxy-1-(1H-imidazol-1-yl) ethyl]-1-methyl-4-phenyl-2(1H)-quinolinone;

4-(3-chlorophenyl)-6-[1-(4-chlorophenyl)-1-(1H-imidazol-1-yl)ethyl]-1-mehtyl-2(1)-quinolinone;

4-(3-chlorophenyl)-6-[1-(4-chlorophenyl)-1-(5-methyl-1H-imidazol-1-yl)ethyl]-1-methyl-2(1H)-quinolinone;

4-(3-chlorophenyl)-6-[1-(4-chlorophenyl)-2-hydroxy-1-(1H-imidazol-1-yl)ethyl]-1-methyl-2(1H)-quinolinone;

4-(3-chlorophenyl)-6-[(4-chlorophenyl)(1H-imidazol-1-yl)methyl]-1-(2-methoxyethyl)-2(1H)-quinolinone ethanedioate (2:3) monohydrate;

6-[(4-chlorophenyl)(1H-imidazol-1-yl)methyl]-4-(1,3-benzodioxol-5-yl)-1-methyl-2(1H)-quinolinone ethanedioate (1:1); a stereoisomeric form thereof or a pharmaceutically acceptable acid or base addition salts thereof.

7. A pharmaceutical composition comprising pharmaceutically acceptable carriers and as an active ingredient a therapeutically effective amount of a compound as claimed in claim 1.

8. A process of preparing a pharmaceutical composition as claimed in claim 7 wherein the pharmaceutically acceptable carriers and the compounds are intimately mixed.

9. A compound of formula (XVI) wherein the radicals R$^2$, R$^3$, R$^4$, R$^5$, R$^6$, R$^7$, R$^8$, R$^{10}$ and R$^{11}$ are as defined in claim 1, or a pharmaceutically acceptable acid addition salt thereof.

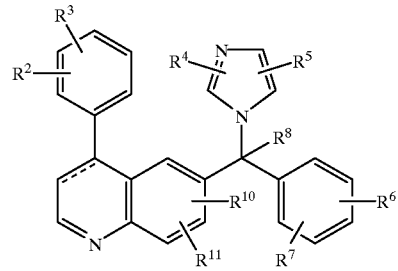

(XVI)

10. A compound of formula (XV) wherein the radicals R$^2$, R$^3$, R$^4$, R$^5$, R$^6$, R$^7$, R$^8$, R$^{10}$ and R$^{11}$ are as defined in claim 1, or a pharmaceutically acceptable acid addition salt thereof.

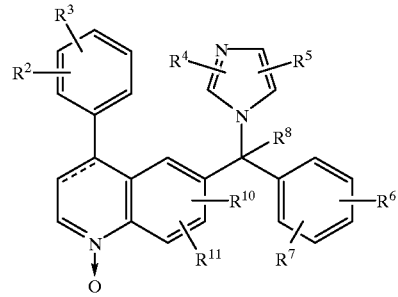

(XV)

11. A process for preparing a compound as claimed in claim 1, characterized by a) N-alkylating an imidazole of formula (II) or an alkali metal salt thereof with a derivative of formula (III);

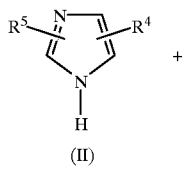

(II)

-continued

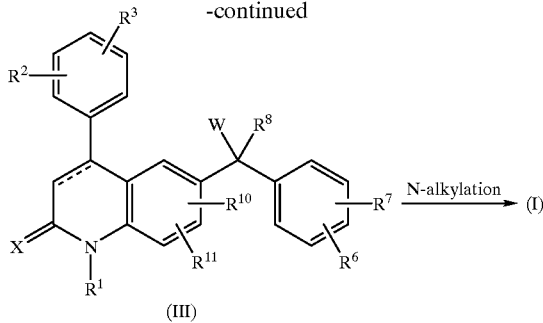
(III)

b) reacting an intermediate of formula (IV) with a reagent of formula (V), wherein Y is either carbon or sulfur, such as, for example, a 1,1'-carbonyl-bis[1H-imidazole];

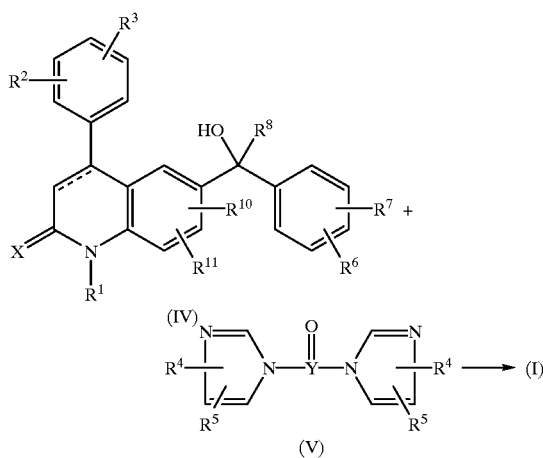

c) by cyclizing an intermediate of formula (VI) thus obtaining compounds of formula (I-a), defined as a compound of formula (I) wherein the dotted line is a bond, may also be obtained;

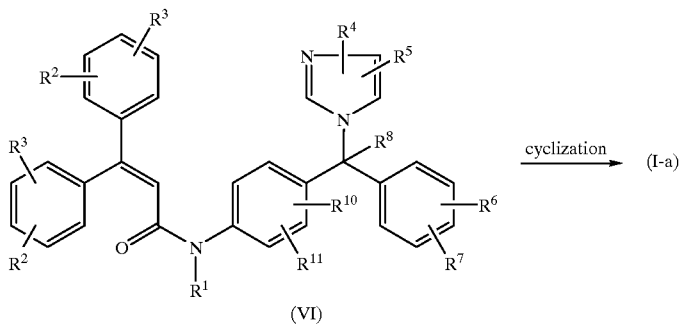

d) hydrolysing an intermediate of formula (XXVI), wherein R is $C_{1-6}$alkyl, in an aqueous acid solution, yielding a compound of formula (I-a-1) defined as a compound of formula (I-a) wherein $R^1$ is hydrogen;

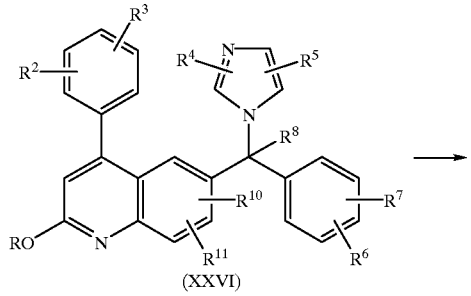
(XXVI)

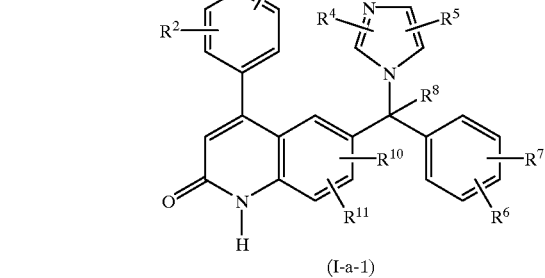
(I-a-1)

e) by opening an epoxide of formula (VIII) with an imidazole of formula (II) thus obtaining a compound of formula (I-b), defined as a compound of formula (I) wherein $R^8$ is hydroxymethylene;

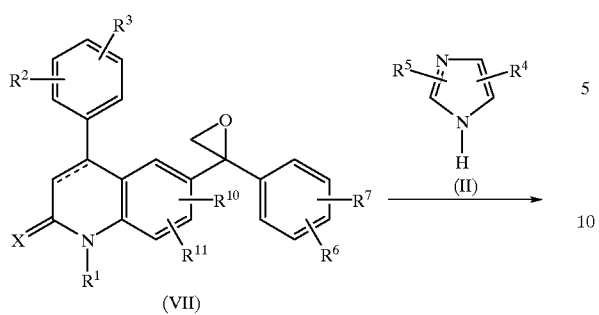

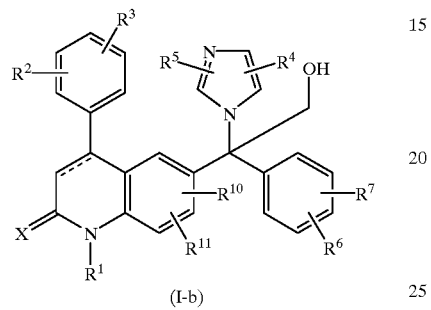

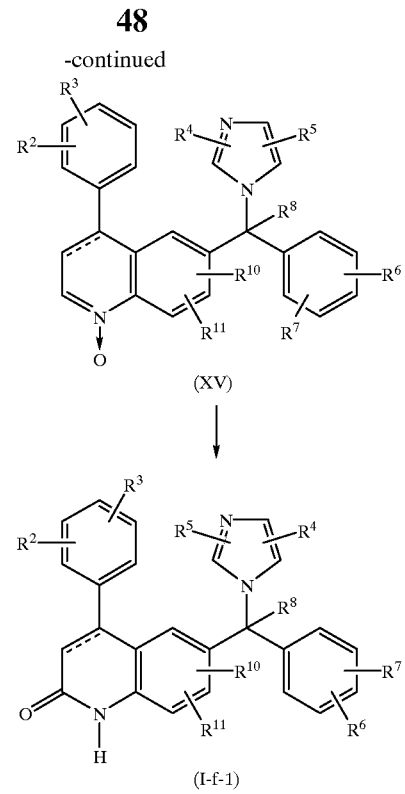

f) transforming intermediate nitrones of formula (XV), prepared by N-oxidizing quinoline derivatives of formula (XVI), either by esterformation and subsequent hydrolysis or via a intramolecular photochemical rearrangement, thus yielding compounds of formula (I-f-1);

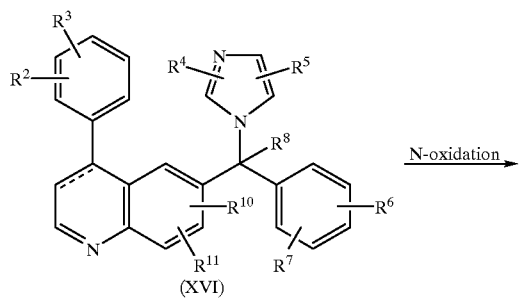

or, if desired, converting a compound of formula (I) into a pharmaceutically acceptable acid addition salt, or conversely, converting an acid addition salt into a free base form with alkali; and/or preparing sterochemically isomeric forms thereof.

12. A method of inhibiting the abnormal growth of cells in a mammal in need thereof comprising administering to the mammal an effective amount of a compound of claim 1.

13. A method of inhibiting tumor growth in a mammal in need thereof comprising administering to the mammal an effective amount of a compound of claim 1.

* * * * *